(12) United States Patent
 Chu et al.

(10) Patent No.: US 8,858,578 B2
(45) Date of Patent: Oct. 14, 2014

(54) MEDICAL IMPLANT

(75) Inventors: Michael S. H. Chu, Brookline, MA (US); Alfred Intoccia, Amherst, NH (US); Michael G. McGrath, Hudson, MA (US); Jozef Slanda, Milford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 40 days.

(21) Appl. No.: 13/243,743

(22) Filed: Sep. 23, 2011

(65) Prior Publication Data

US 2012/0016370 A1    Jan. 19, 2012

Related U.S. Application Data

(63) Continuation of application No. 10/640,838, filed on Aug. 14, 2003, now Pat. No. 8,033,983, and a continuation-in-part of application No. 10/093,371, filed on Mar. 7, 2002, now Pat. No. 6,991,597, which is a continuation-in-part of application No. 10/093,398, filed on Mar. 7, 2002, now Pat. No. 8,162,816, which is a continuation-in-part of application No. 10/093,424, filed on Mar. 7, 2002, now Pat. No. 6,936,052, which is a continuation-in-part of application No. 10/093,450, filed on Mar. 7, 2002, now Pat. No. 8,617,048, which is a continuation-in-part of application No. 10/093,498, filed on Mar. 7, 2002, now Pat. No. 7,025,772, which is a continuation-in-part of application No. 10/094,352, filed on Mar. 7, 2002, now Pat. No. 7,235,043.

(60) Provisional application No. 60/274,843, filed on Mar. 9, 2001, provisional application No. 60/268,863, filed on Apr. 26, 2001, provisional application No. 60/403,555, filed on Aug. 14, 2002.

(51) Int. Cl.
| A61B 17/08 | (2006.01) |
| A61F 2/00 | (2006.01) |
| A61F 2/02 | (2006.01) |
| A61B 17/00 | (2006.01) |
| A61B 17/06 | (2006.01) |
| A61B 17/34 | (2006.01) |

(52) U.S. Cl.
CPC . *A61B 17/00234* (2013.01); *A61B 2017/06171* (2013.01); *A61B 2017/06076* (2013.01); *A61B 17/3468* (2013.01); *A61B 2017/06042* (2013.01); *A61F 2/0063* (2013.01); *A61B 17/06109* (2013.01); *A61B 2017/06019* (2013.01); *A61B 2017/06052* (2013.01); *A61B 2017/00805* (2013.01); *A61F 2/0045* (2013.01)
USPC ................ 606/151; 600/37; 623/23.72

(58) Field of Classification Search
USPC .......... 606/191–193, 151; 600/37; 623/23.72; 602/54, 57
See application file for complete search history.

(56) References Cited

U.S. PATENT DOCUMENTS

| 3,245,855 | A | * | 4/1966 | Stenvall | 156/152 |
| 4,235,337 | A | * | 11/1980 | Dotta | 206/441 |
| 4,418,822 | A | * | 12/1983 | Dotta | 206/441 |

(Continued)

*Primary Examiner* — Julian W Woo

(57) ABSTRACT

A medical assembly includes an implant and an envelope at least partially enclosing a portion of the implant. The envelope may include a tongue to protect the implant, a scaffold to provide integrity to the envelope, a tab access to ease envelope withdrawal, and/or one or more discontinuities to ease envelope withdrawal.

9 Claims, 24 Drawing Sheets

(56) References Cited

U.S. PATENT DOCUMENTS

| | | | |
|---|---|---|---|
| 5,899,909 A * | 5/1999 | Claren et al. | 606/119 |
| 6,273,852 B1 * | 8/2001 | Lehe et al. | 600/30 |
| 6,423,080 B1 * | 7/2002 | Gellman et al. | 606/148 |
| 6,475,139 B1 * | 11/2002 | Miller | 600/135 |
| 6,478,727 B2 * | 11/2002 | Scetbon | 600/30 |
| 6,491,703 B1 * | 12/2002 | Ulmsten | 606/144 |
| 6,612,977 B2 * | 9/2003 | Staskin et al. | 600/30 |
| 6,641,525 B2 * | 11/2003 | Rocheleau et al. | 600/30 |
| 6,652,450 B2 * | 11/2003 | Neisz et al. | 600/30 |
| 6,685,626 B2 * | 2/2004 | Wironen | 600/37 |
| 6,685,629 B2 * | 2/2004 | Therin | 600/37 |
| 6,702,827 B1 * | 3/2004 | Lund et al. | 606/151 |
| 6,719,137 B2 * | 4/2004 | Dotta | 206/441 |
| 6,971,986 B2 * | 12/2005 | Staskin et al. | 600/30 |
| 6,991,597 B2 * | 1/2006 | Gellman et al. | 600/37 |
| 7,025,772 B2 * | 4/2006 | Gellman et al. | 606/151 |
| 7,070,558 B2 * | 7/2006 | Gellman et al. | 600/37 |
| 7,083,637 B1 * | 8/2006 | Tannhauser | 606/228 |
| 7,131,943 B2 * | 11/2006 | Kammerer | 600/30 |
| 7,235,043 B2 * | 6/2007 | Gellman et al. | 600/29 |
| 8,033,983 B2 * | 10/2011 | Chu et al. | 600/37 |
| 8,162,816 B2 * | 4/2012 | Gellman et al. | 600/37 |
| 2002/0151909 A1 * | 10/2002 | Gellman et al. | 606/139 |
| 2002/0161382 A1 * | 10/2002 | Neisz et al. | 606/151 |
| 2004/0015048 A1 * | 1/2004 | Neisz et al. | 600/37 |
| 2004/0073234 A1 * | 4/2004 | Chu et al. | 606/151 |
| 2005/0043580 A1 * | 2/2005 | Watschke et al. | 600/30 |
| 2006/0195013 A1 * | 8/2006 | Gellman et al. | 600/37 |
| 2010/0222641 A1 * | 9/2010 | Chu et al. | 600/30 |
| 2012/0016370 A1 * | 1/2012 | Chu et al. | 606/93 |

* cited by examiner

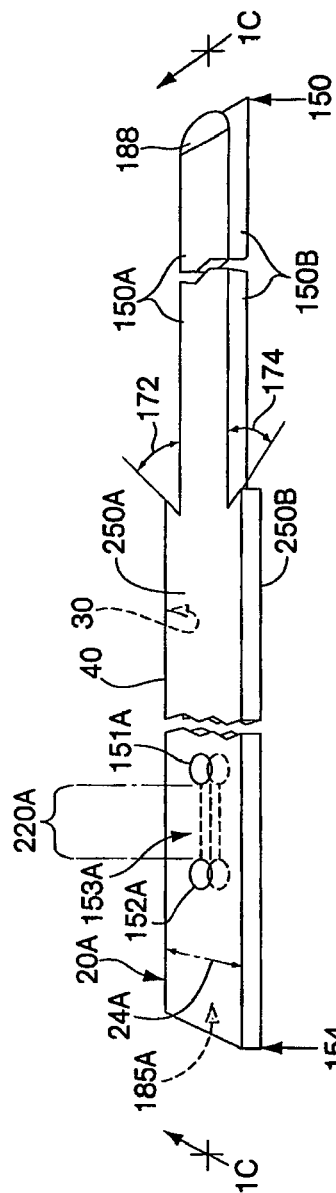
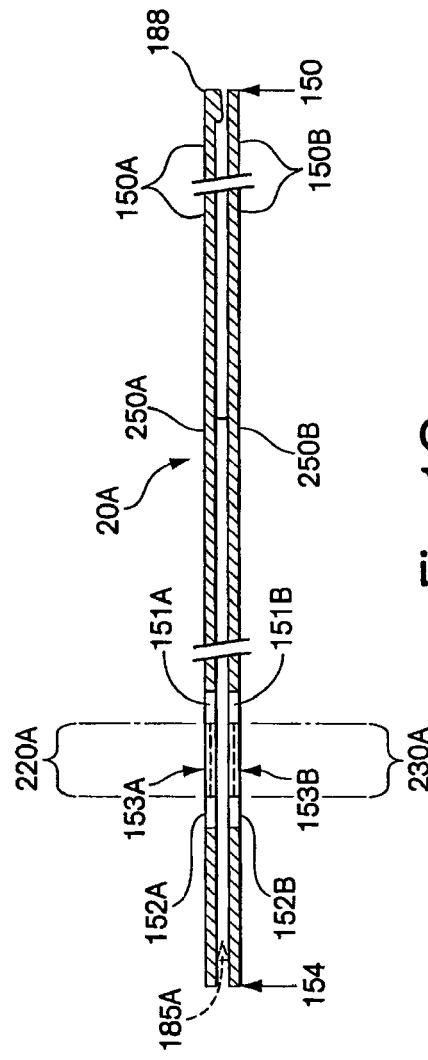
Fig. 1B
Fig. 1C

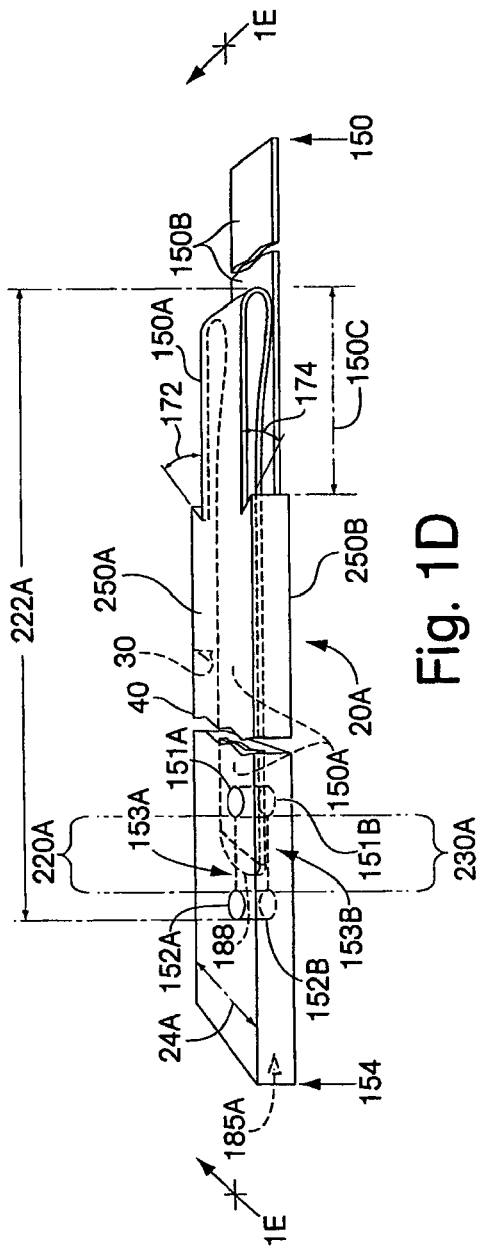
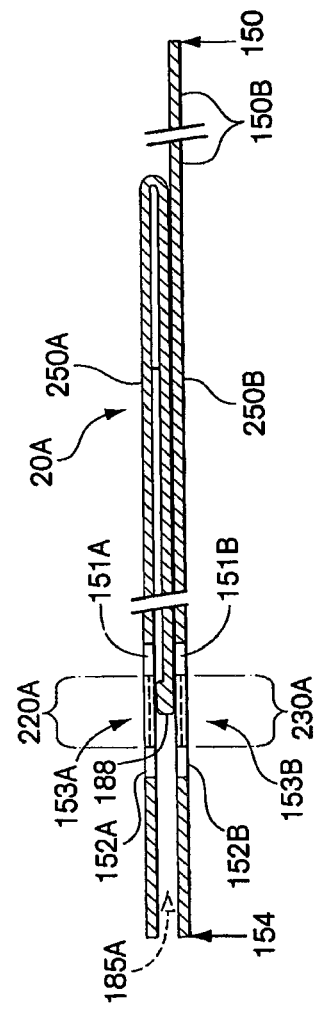
Fig. 1D
Fig. 1E

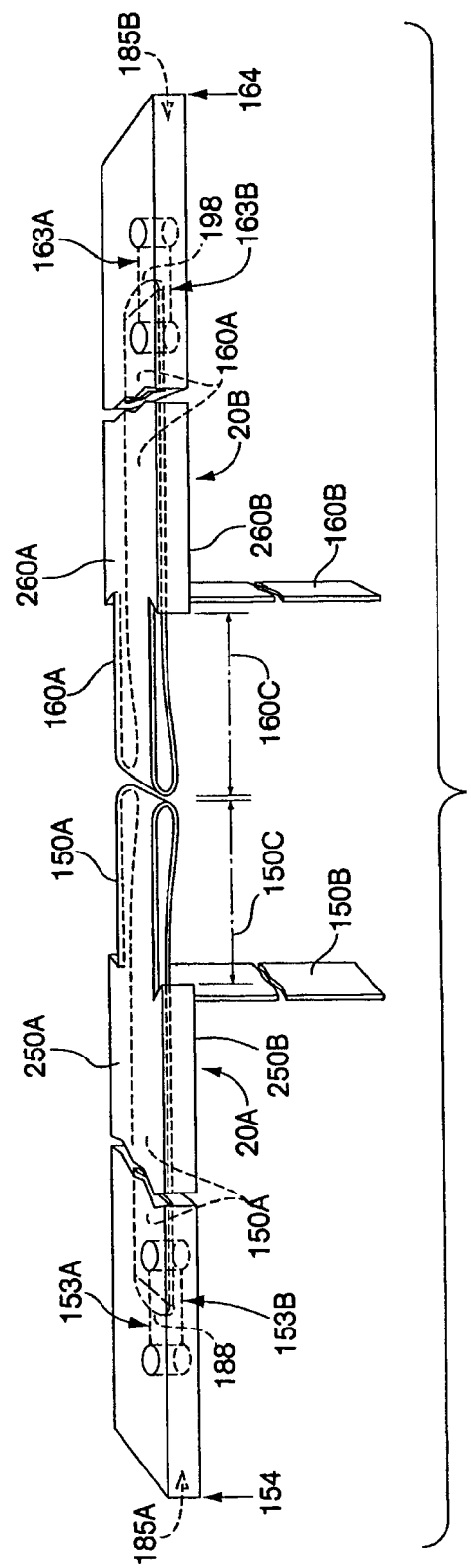

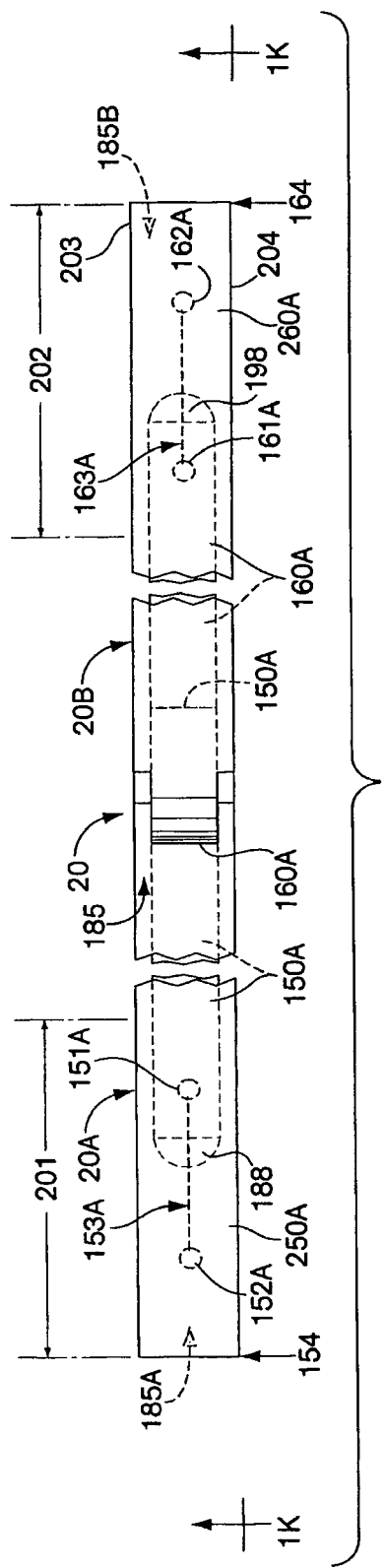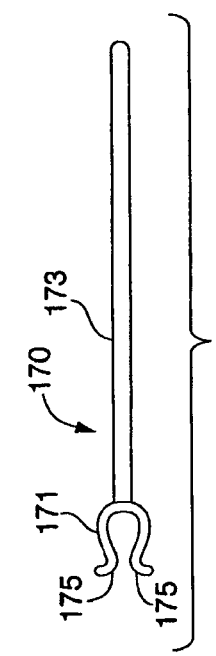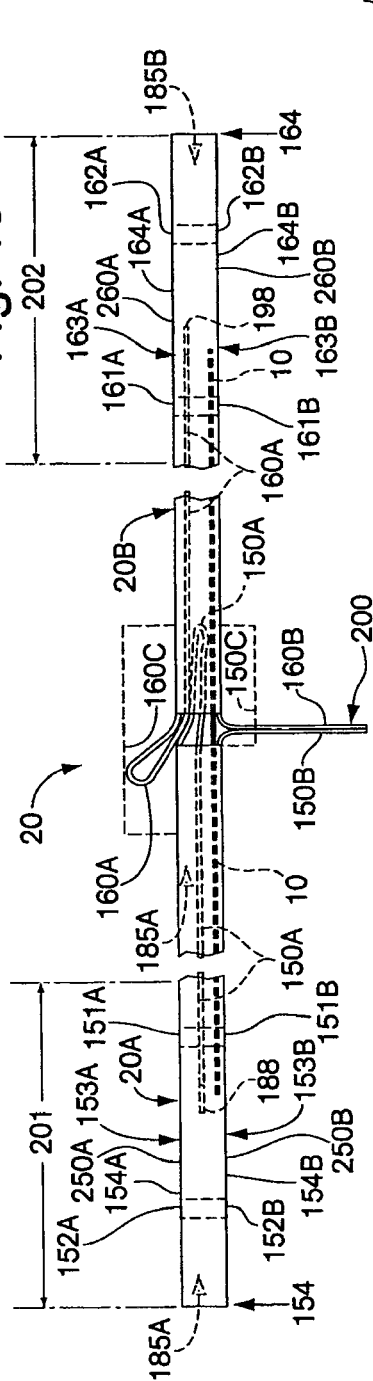

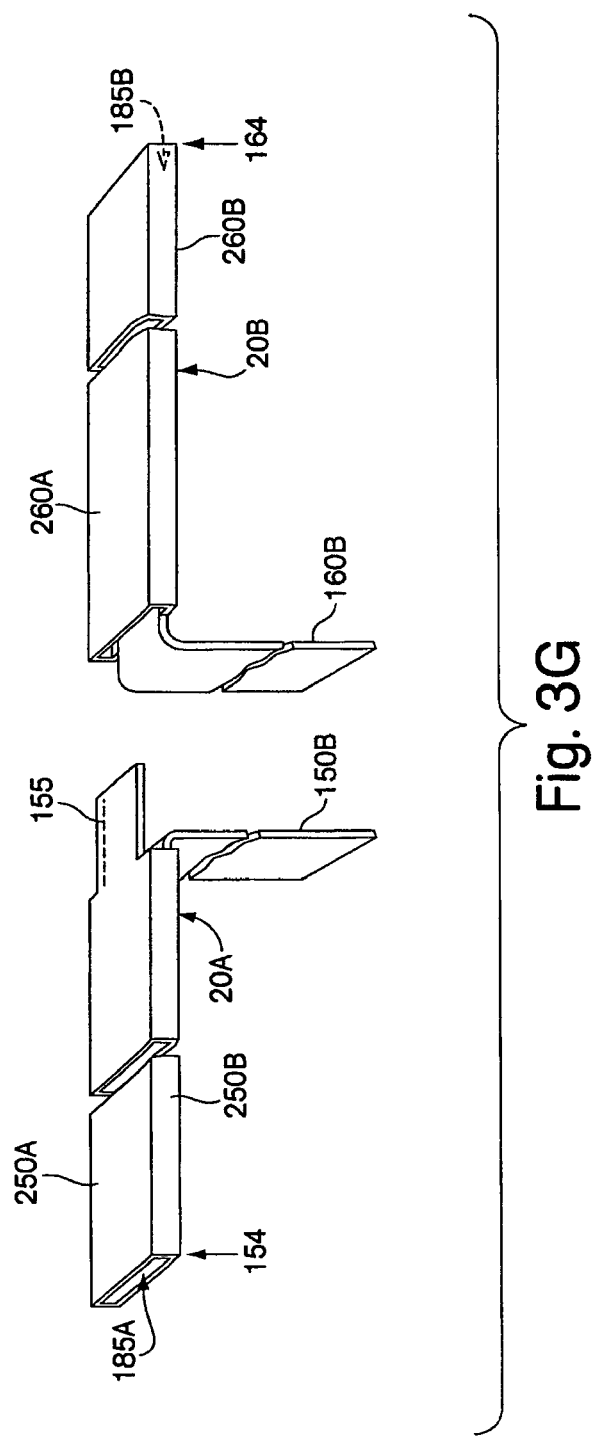

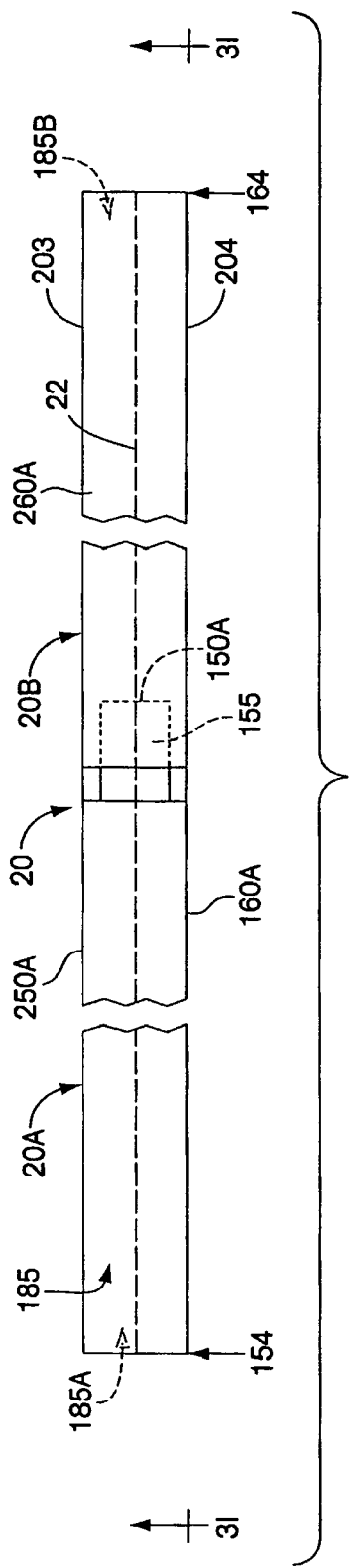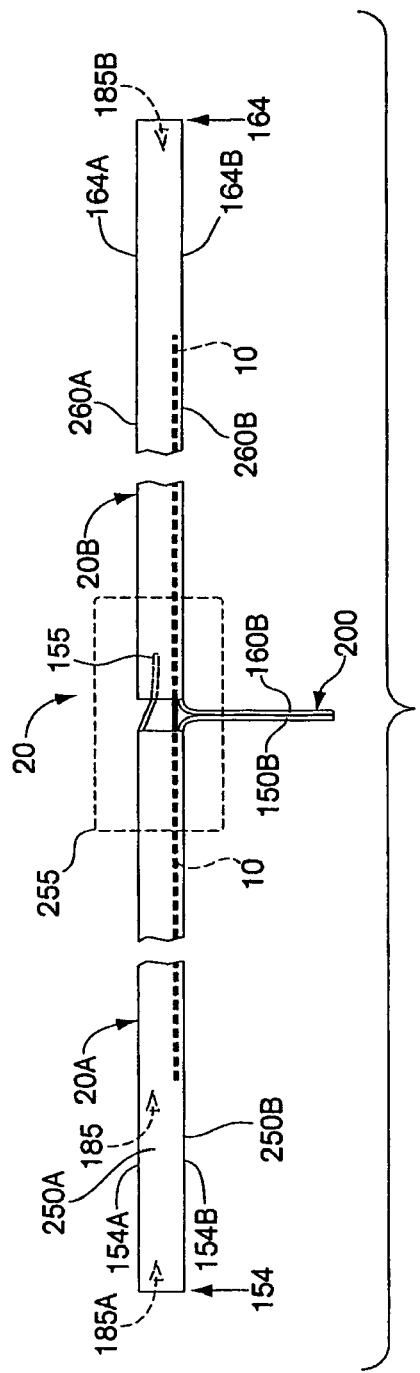

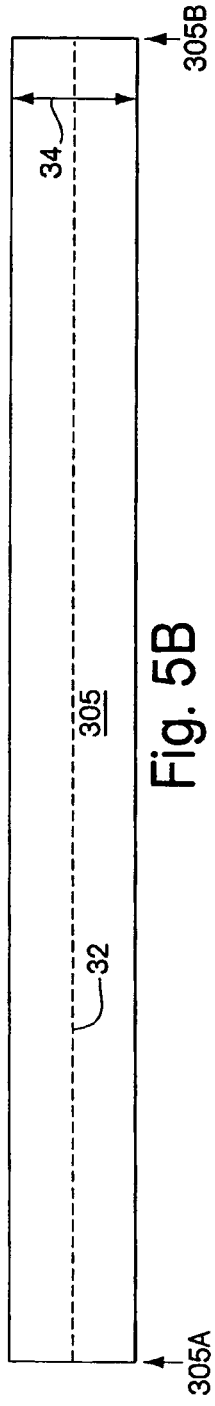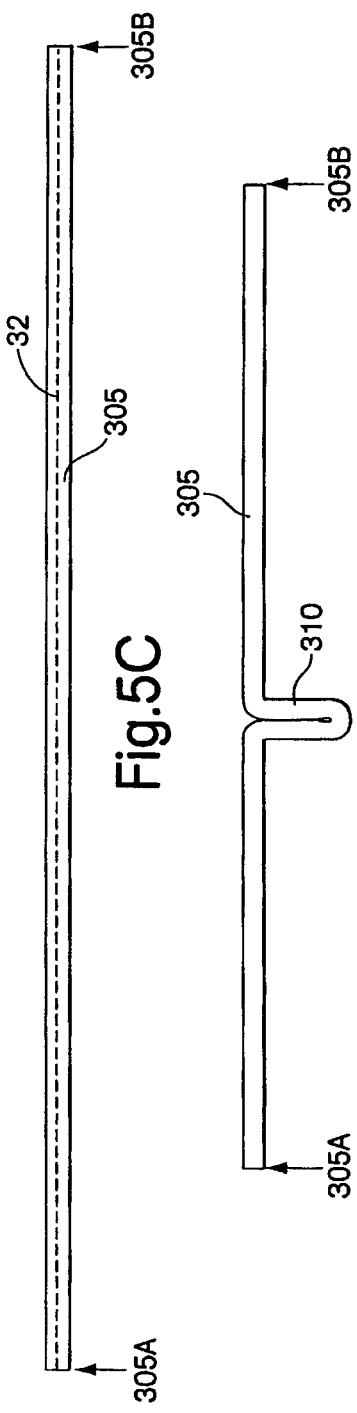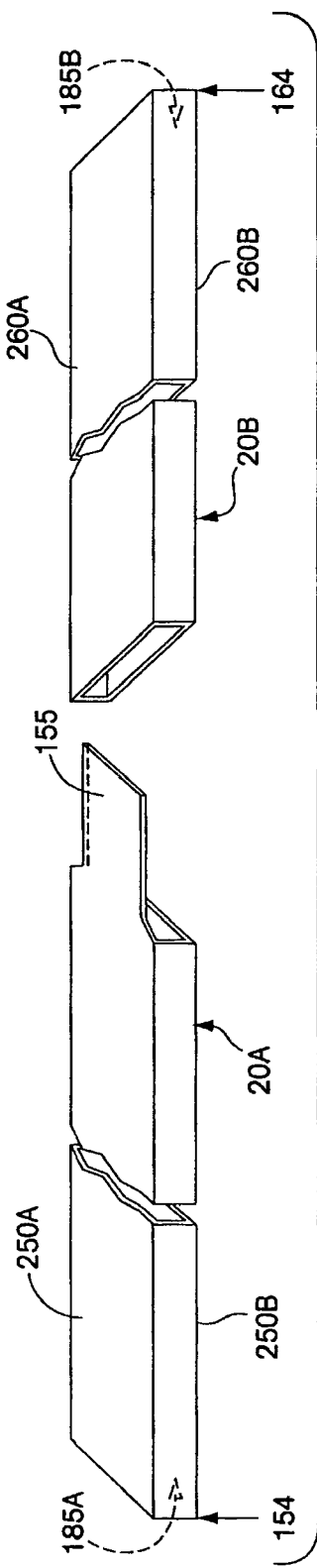

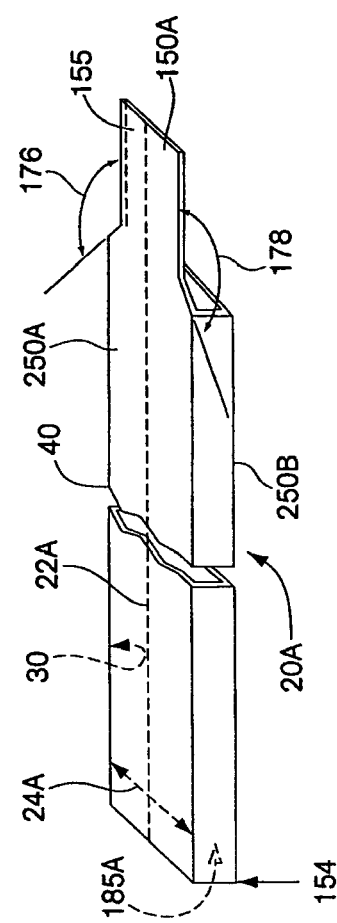

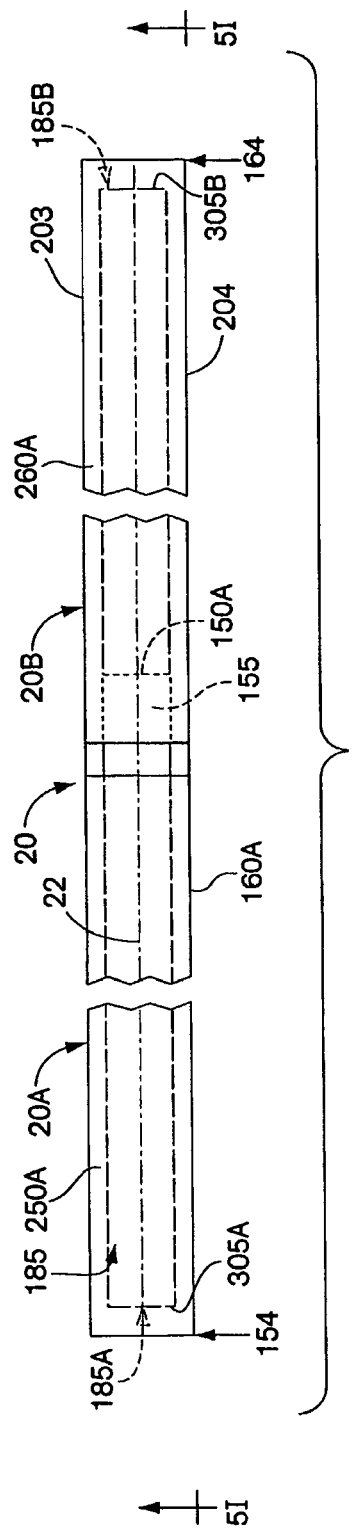
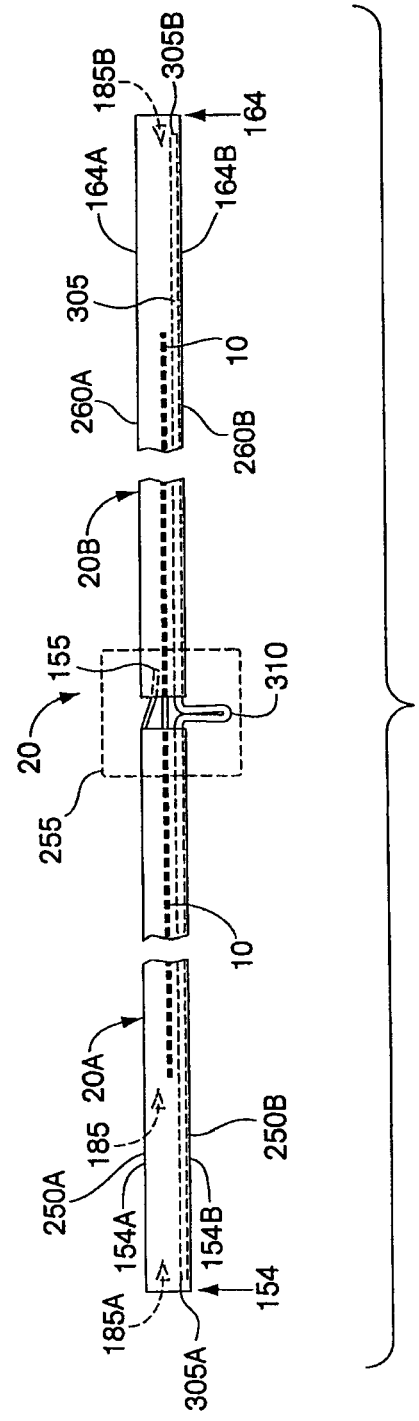

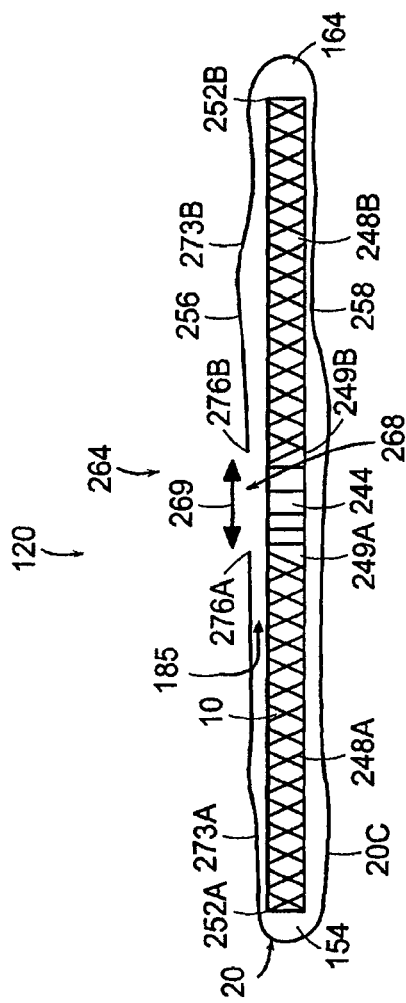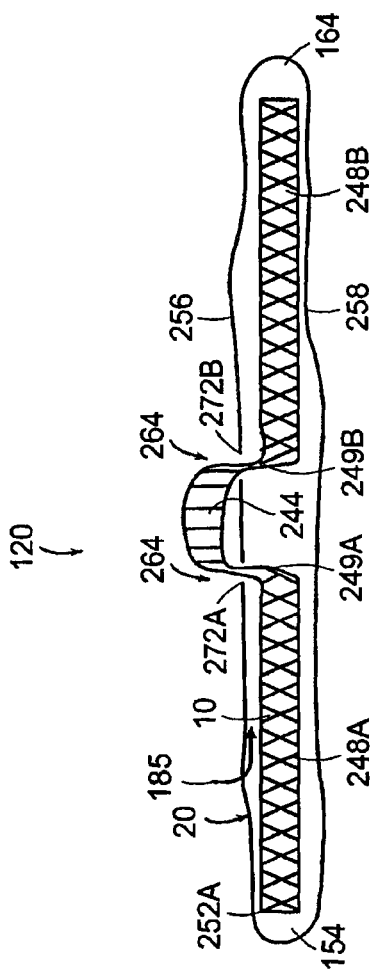

MEDICAL IMPLANT

CROSS-REFERENCE TO RELATED APPLICATIONS

This application is a continuation of U.S. patent application Ser. No. 10/640,838 filed in the U.S. patent Office on Aug. 14, 2003 now U.S. Pat. No. 8,033,983, which is based on and claims priority to provisional patent application Ser. No. 60/403,555 filed in the U.S. Patent Office on Aug. 14, 2002 and provisional patent application Ser. No. 60/449,465 filed in the U.S. Patent Office on Feb. 24, 2003. The entire contents of each of these two provisional applications are incorporated by reference herein. This application is a continuation-in-part application of U.S. patent application Ser. No. 10/093,371 filed in the U.S. Patent Office on Mar. 7, 2002, now U.S. Pat. No. 6,991,597, Ser. No. 10/093,398 filed in the U.S. Patent Office on Mar. 7, 2002, Ser. No. 10/093,424 filed in the U.S. Patent Office on Mar. 7, 2002, now U.S. Pat. No. 6,936,052, Ser. No. 10/093,450 filed in the U.S. Patent Office on Mar. 7, 2002, Ser. No. 10/093,498 filed in the U.S. Patent Office on Mar. 7, 2002, now U.S. Pat. No. 7,025,772, and Ser. No. 10/094,352 filed in the U.S. Patent Office on Mar. 7, 2002, now U.S. Pat. No. 7,235,043, which claim benefit of and priority to provisional patent application Ser. No. 60/274,843 filed in the U.S. Patent Office on Mar. 9, 2001 and provisional patent application Ser. No. 60/286,863 filed in the U.S. Patent Office on Apr. 26, 2001. The entire contents of these six nonprovisional applications are incorporated by reference herein.

TECHNICAL FIELD

The invention relates generally to implanting a device such as a surgical sling at an anatomical site in the body of a mammal. More particularly, the invention relates to delivering and placing the surgical sling (entirely or partially within an envelope or a sheath) at an anatomical site in the body of a female patient or a male patient.

BACKGROUND INFORMATION

It is known to use a surgical sling to repair and restore living tissue. For example, surgical slings may be used to support and/or reinforce a damaged or weakened portion in the body of a patient. A sling used for such a purpose generally is made sufficiently porous to allow for growth of tissue through the mesh after implantation. The healing tissue grows through openings in, for example, an implanted synthetic mesh, thereby assimilating the tissue with the mesh and adding structural integrity to the tissue.

Surgical slings may be produced with yarns including monofilament and multifilament yarns. Multifilament yarns have small void areas or interstitial spaces between the yarn filaments. The yarns in the surgical sling may be made of materials such as polypropylene and polyesters.

SUMMARY OF THE INVENTION

The crevices and voids of a surgical sling may harbor bacteria or other pathogens that contaminate the surgical sling during implantation. Following implantation of the surgical sling in the patient, the bacteria or other pathogens harbored in the sling are introduced to the anatomical site where the sling is implanted. Typically, the anatomical site being repaired is poorly accessible to antimicrobial drugs applied intraoperatively to combat bacteria or other pathogens that may be picked up and introduced to the anatomical site during the surgery to implant the mesh.

The invention relates to an implant, such as a surgical sling or mesh, for implantation at an anatomical site in the body of a patient, such as at the mid-urethra. The implant can be disposed within an envelope or a sheath for delivery to and placement at the anatomical site, and such a combination (of an implant and an envelope) is referred to herein as an implant assembly. Implants and implant assemblies according to the invention are relatively inexpensive, provide effective therapy, and require minimal training before use. Implants and implant assemblies according to the invention can be used to treat female urinary incontinence, including stress incontinence, for example. The invention also relates generally to methods of making and using implants and implant assemblies.

The invention, in one embodiment, addresses deficiencies in the prior art by providing an implant assembly that reduces or prevents contamination of the implant and contamination of the patient's tissue during delivery of the implant assembly to the anatomical site. An operator can adjust and position the implant assembly at the anatomical site in the patient's body and maintain the correct position of the implant at the anatomical site during and after withdrawal of an envelope, which at least partially encloses the implant. Also, the implant or implant assembly can be easily associated with a delivery device. The delivery device can be used to position the implant assembly (such as a sling in an envelope) at the patient's urethra. Transvaginal, transabdominal (e.g., percutaneous), supra-pubic, pre-pubic, or transobturator approaches can be used to install and position the implants and the implant assemblies. Without limitation, exemplary delivery devices and methodologies that may be employed in combination with the implant assemblies of the invention can be found in U.S. patent application Ser. Nos. 10/093,498, 10/093,398, 10/093,450, 10/093,371, 10/094,352, and 10/093,424 filed in the United States Patent Office on Mar. 7, 2002, U.S. provisional patent application Ser. No. 60/418,827 filed in the United States Patent Office Oct. 15, 2002, U.S. provisional patent application Ser. No. 60/418,642 filed in the United States Patent Office Oct. 15, 2002, and U.S. provisional patent application Ser. No. 60/434,167 filed in the United States Patent Office Dec. 17, 2002, the disclosures of which are incorporated herein by reference.

The U.S. patent application Ser. No. 10/641,170 filed Aug. 14, 2003, entitled "Medical Slings" by Rao et al., the U.S. patent application Ser. No. 10/642,395 filed Aug. 14, 2003, U.S. patent application Ser. No. 10/642,397 filed Aug. 14, 2003, U.S. patent application Ser. No. 10/642,365 filed Aug. 14, 2003, and U.S. patent application Ser. No. 10/641,487 filed Aug. 14, 2003, all entitled "Systems, Methods and Devices Relating to Delivery of Medical Implants" by Chu et al., the U.S. patent application Ser. No. 10/641,192 filed Aug. 14, 2003, entitled "Medical Slings" by Chu, the U.S. patent application Ser. No. 10/641,376 filed Aug. 14, 2003, entitled "Spacer for Sling Delivery System" by Chu et al., and the Provisional patent application No. 60/495,439 filed Aug. 14, 2003, entitled "Surgical Slings" by Li et al. are all filed on even date herewith and are incorporated herein by reference in their entirety.

In one aspect, the invention provides an assembly for delivering an implant to an anatomical location in a body. According to this aspect, the assembly includes an envelope having two sleeves. The two sleeves of the envelope enclose the implant, such as a sling for the treatment of female urinary incontinence. In one embodiment, the assembly further includes a scaffold. The scaffold is sized and shaped to be enclosed within a lumen of the envelope. The scaffold is configured to couple the first sleeve and the second sleeve together. In one embodiment, each of the sleeves of the envelope is about the same length. In another embodiment, the scaffold includes a fold to form a hinge between the first and second sleeves. The scaffold may be manufactured, for example, from rigid or flexible materials.

In another aspect of the invention, at least one sleeve of the envelope includes a tongue, which overlaps at least a portion of the implant enclosed within the envelope. In one embodiment of this aspect of the invention, the tongue of the first sleeve is positioned within the lumen of the second sleeve. In some configurations, the tongue is an integral part of at least one sleeve.

In another aspect, the assembly includes a tab joined to the envelope. The tab may be a positioning member for positioning the implant in the body of the patient. In one embodiment of this aspect of the invention, the envelope includes a first sleeve section and a second sleeve section which interoperate to enclose at least a portion of the implant. A tab on the end of the first sleeve section is passed through the first sleeve section to a first end of the envelope. A tab access for accessing the tab is located at the first end of the envelope. The tab is accessible through the tab access to position the implant in the patient's body. Similarly, a tab on the end of the second sleeve section is passed through the second sleeve section to a second end of the envelope and the tab is accessible through a tab access located at the second end of the envelope. In one embodiment, the tab access is a linear cut through at least one sleeve from the outside of the sleeve, into the lumen of the sleeve. Alternatively, the tab access is a perforation or a series of perforations through the sleeve.

In another aspect, the assembly includes an envelope with one or more sleeves having a first side and a second side. The envelope encloses at least a portion of an implant, for example, a sling having a length and a width. The first side of the envelope includes at least one discontinuity that exposes the width along a first portion of the sling. In one embodiment, the discontinuity is a gap disposed between the first and second portions of the first side of the envelope. The mid-length portion of the sling is devoid of covering (e.g., not enclosed) by the envelope. This mid-length portion of the sling may be de-tanged. In another embodiment, the first side of the envelope has a first slit-shaped aperture and a second slit-shaped aperture. The first and second slit-shaped apertures may be intermediately located along the length of the sling. The sling that is at least partially enclosed by the envelope threads out of the envelope through the first slit-shaped aperture and threads back into the envelope through the second slit-shaped aperture, which creates a mid-length envelopeless sling loop that is external to the envelope. The mid-length envelopeless sling loop may be de-tanged and is devoid of covering, e.g., external to the envelope.

Additional embodiments of the assembly according to the invention include at least one loading member included on an end of an envelope. The loading member facilitates interoperability of the envelope with a delivery device. The loading member may be bonded to the implant, the envelope, the scaffold, or some combination. The loading member may be, for example, a guide member, a guide tube, or some other type of male or female structure (such as a hook, loop, etc.) disposed at an end of the envelope for mating with a complementary structure on the delivery device. At least one of the sleeves of the envelope may be manufactured from a composite of two or more materials. In one embodiment, the two sleeves of the invention are joined by a hinge. The envelope of the delivery device may include a visual indication mark, for example, a spacer, a clamp, a tinted area or other indication mark that provides a visual indication of the placement of the sling delivery device, i.e., the envelope and/or implant. The visual indication may be employed to inform the operator about the orientation of, for example, the sling.

In another aspect, the invention relates to a method for delivering an implant assembly in a patient's body. In one embodiment, an assembly is provided that includes an envelope having at least two sleeves that enclose at least a portion of the implant. In a further embodiment, the assembly includes a scaffold that is sized and shaped to fit within the lumen of the envelope. In another embodiment of this aspect of the invention, at least one of the sleeves has a tongue portion that overlaps the implant. In yet another embodiment, the assembly includes an envelope having at least one tab passed through a sleeve section to an end of the envelope and at least one tab access for accessing the tab that is located at an end of the envelope.

In one embodiment, the implant assembly is positioned at the anatomical site in the patient's body. When the operator is satisfied with the position of the implant assembly, the envelope is withdrawn from the patient's body. The envelope may be withdrawn from the patient's body by pulling the tabs and pulling the hinge and the remaining portions of the envelope from the body of the patient. Preferably, the implant assembly is positioned at the mid urethra and a tab on a first sleeve section of an envelope is pulled through the tab access on an end of the envelope. The pulled tab tears a portion of the envelope away from the implant and a hinge section is pulled intravaginally to withdraw the envelope from a patient's body. The envelope may also be withdrawn by cutting the tab accesses, separating the envelope into two sides along the cut tab access, accessing the internal tabs, pulling the internal tabs, and pulling the hinge and remaining portions of the envelope intravaginally from the body of the patient via the vagina. In another embodiment, the envelope may be withdrawn by cutting the hinge section and separating the first sleeve from the second sleeve. Alternatively, the envelope may be withdrawn by cutting the scaffold and separating the first sleeve from the second sleeve. In another embodiment, the envelope may be withdrawn by cutting and separating the external tabs or the loading members, separating the first sleeve from the second sleeve and scaffold, separating the second sleeve from the scaffold, then pulling the scaffold from the body of the patient. After withdrawal of the envelope, the implant remains where it was positioned at the anatomical site, for example, at the mid-urethra of the patient to treat female urinary incontinence.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 1B illustrates an embodiment of one of the sleeves illustrated in FIG. 1A.

FIG. 1C illustrates a cross section at 1C-1C of the embodiment of the sleeve illustrated in FIG. 1B.

FIG. 1D illustrates an embodiment of one of the sleeves illustrated in FIG. 1A.

FIG. 1E illustrates a cross section at 1E-1E of the embodiment of the sleeve illustrated in FIG. 1D.

FIG. 1H illustrates one embodiment of a method for making the assembly for delivering an implant to a body illustrated in FIG. 1A.

FIG. 1I illustrates a top view of one embodiment of an assembly for delivering an implant to a body illustrated in FIG. 1A.

FIG. 1J illustrates one embodiment of a placement fork according to the invention.

FIG. 1K illustrates a cross section at 1K-1K of an embodiment of the assembly for delivering an implant to a body illustrated in FIG. 1I.

FIGS. 3B-3G illustrate one embodiment of a method of making an assembly for delivering an implant to a body illustrated in FIG. 3A.

FIG. 3H illustrates a top view of one embodiment of the assembly for delivering an implant to a body illustrated in FIG. 3A.

FIG. 3I illustrates a cross-section at 3I-3I of one embodiment of the assembly for delivering an implant to a body illustrated in FIG. 3H.

FIG. 5B illustrates a top view of one embodiment of a scaffold for use in the assembly illustrated in FIG. 5A for delivering an implant to a body.

FIG. 5C illustrates a side view of the scaffold illustrated in FIG. 5B.

FIG. 5D illustrates another embodiment of the scaffold for use in the assembly illustrated in FIG. 5A.

FIG. 5E illustrates another embodiment of one of the sleeves illustrated in FIG. 5A.

FIG. 5G illustrates one embodiment of a method of making the assembly for delivering an implant to a body illustrated in FIG. 5A.

FIG. 5H illustrates a top view of one embodiment of the assembly for delivering an implant to a body illustrated in FIG. 5A.

FIG. 5I illustrates a cross-section at 5I-5I of one embodiment of the assembly for delivering an implant to a body illustrated in FIG. 5H.

FIG. 6 illustrates a fragmented plan view of another embodiment of an assembly for delivering an implant to a body.

FIG. 7 illustrates a fragmented plan view of another embodiment of an assembly for delivering an implant to a body.

DESCRIPTION

Figure 1A:
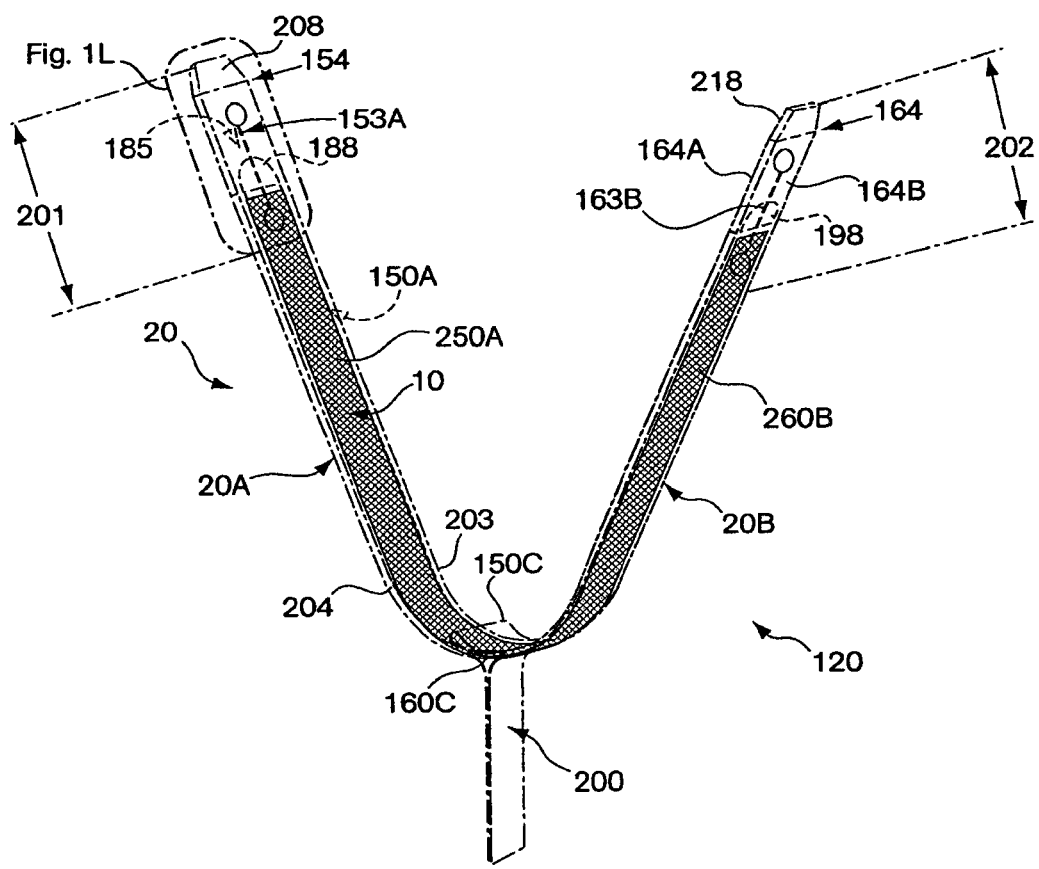
FIG. 1A illustrates one embodiment of an assembly for delivering an implant to a body.

In general, the invention described herein is an assembly for implanting an implant into the body of a patient. Referring to FIGS. 1A, 2A, 3A, 4, 5A, 6, and 7 in one aspect, the assembly 120 includes an envelope 20 enclosing an implant for example a sling 10. In accordance with the assembly 120 of the invention, an implant (for example, a surgical sling 10 formed from a mesh or other suitable material) can be entirely surrounded by or enclosed within the envelope 20, or only partially covered by the envelope 20.

In one embodiment according to the invention, the implant is a surgical mesh. The surgical sling 10 may be fabricated from one or more yarns and the yarns may be made from one or more materials. Materials that may be employed include polypropylene, polyesters, polyolefins, polytetrafluoroethylene, polyethylene, polyurethanes, nylons, and co-polymers, without limitation such as those described in U.S. Pat. No. 6,042,592, the entirety of which is incorporated by reference herein. The sling 10 may also be a hybrid of synthetic materials and tissues. The sling 10 may also be made from absorbable materials, such as, polyglycolic acid, polylactic acid and other suitable absorbable materials. Exemplary slings 10 that may be employed with the invention are described in, for example, U.S. patent application Ser. No. 09/916,983 filed Jul. 27, 2001, provisional patent application Ser. No. 60/388,109 filed Jun. 12, 2002, U.S. patent application Ser. No. 10/460,112 filed Jun. 12, 2003, U.S. patent application Ser. No. 10/092,872 filed Mar. 7, 2002, provisional patent application Ser. No. 60/449,465 filed Feb. 24, 2003, and provisional patent application Ser. No. 60/465,722 filed Apr. 25, 2003 the entirety of all of which are incorporated by reference herein. Other exemplary slings 10 that may be employed with the invention are described in the U.S. patent application Ser. No. 10/641,170 filed Aug. 14, 2003, entitled "Medical Slings" by Rao et al., and U.S. patent application Ser. No. 10/641,192 filed Aug. 14, 2003, entitled "Medical Slings" by Chu, filed on even date herewith, the entirety of both of which are incorporated herein by reference.

The assembly 120 of the invention, which includes the envelope 20 and the sling 10, may further include one ore more spacers (not shown). Exemplary spacers that may be employed with the invention are described, for example, in provisional patent application Ser. No. 60/434,167 filed Dec. 17, 2002, provisional patent application Ser. No. 60/449,465 filed Feb. 24, 2003 and in the U.S. patent application Ser. No. 10/641,376, filed Aug. 14, 2003, entitled "Spacer for Sling Delivery System" by Chu et al. filed on even date herewith, the entirety of all of which are incorporated herein by reference.

Each of the one or more yarns used to make the sling 10 may include a plurality of filaments. Alternatively, a monofilament yarn may be employed. In one embodiment, the sling 10 is formed from a mesh and the mesh may be a polypropylene monofilament tricot mesh for use in surgical applications. Within the mesh, each yarn may have void areas between yarn filaments. The process used to fabricate the mesh may create crevices in the mesh. Multifilament yarns have multiple voids or interstitial spaces between the yarn filaments. Mesh, according to the invention, may be produced according to a variety of fabrication processes known to the skilled artisan including, but not limited to, knitting, weaving, or braiding. Meshes fabricated using multifilament yarns may have both crevices and interstitial voids. According to the illustrative embodiment of the invention, the surgical mesh is enclosed within the envelope 20 that entirely or partially surrounds the surgical mesh. The envelope 20 surrounding the mesh reduces the likelihood that the mesh will become contaminated with foreign matter, such as bacteria, during mesh placement at an anatomical site in the body of the patient.

The illustrative envelopes 20 may be of varying construction, for example, the envelope 20 may be used to assist in handling the sling 10 and/or to assist in adjusting the sling 10 during surgical placement. The envelope 20 also aids in preventing the sling 10 from stretching or becoming misshapen due to handling prior to placement at the anatomical site. The envelope 20 may be likened to a pouch or a sleeve that partially or entirely surrounds the sling 10. The thickness of the material used to make the envelope 20 may range from about 0.0001 inch to about 0.01 inch, preferably being about 0.0003 inch thick. In the illustrative embodiment, the envelope 20 defines a lumen 185 through which at least a portion of the sling 10 can pass.

The material used to make the envelope 20 may be selected from the group including polypropylene, polyethylene, polyester, polytetrafluoroethylene (e.g., TEFLON®), TYVEK®, MYLAR®, and co-polymers, thereof. In one embodiment according to the invention, the material used to make the envelope 20 is an absorbent material, such as, for example, a sponge-like material. The envelope 20 may be pre-soaked in a solution containing a drug such as an antibiotic prior to surgical implantation of the implant 10 in a patient's body.

In some configurations sling 10 is made of a non-wettable material such as a polypropylene, polyethylene, polyester, polytetrafluoroethylene, TYVEK available from DuPont, Pa., MYLAR available from DuPont, Pa., or co-polymers thereof. Polytetrafluoroethylene, which is suitable for use in accordance with the present invention, is available from DuPont (Wilmington, Del., under the trade designation TEFLON). Such non-wettable materials do not take up any liquids, for example, therapeutic agents in solution.

To permit therapeutic agents to bond or absorb to these non-wettable material sides, the sling 10 may be treated with a substance that is wettable such as, for example, a wettable coating composition. The wettable coating composition may be a synthetic coating (e.g., polyvinylpyrrlidone or PVP), a natural coating (e.g., collagen) or a physically absorbent material (e.g., sponge comprising cellulose or open celled polyurethane). The wettable coating composition may be hydrophilic. Suitable hydrophilic coatings may be water soluble and include, for example, such coatings available under the trade designations Hydroplus and Hydropass. Similarly, a hydrophobic coating may be employed on one or more surfaces of the sling 10. Suitable hydrophobic coatings that may be employed in accordance with the invention include but are not limited to polytetrafluoroethylene, silicon, and Pyrelene.

Therapeutic agents may also be employed with sling 10. For example, the hydrophilic coating and the therapeutic agent are mixed to form a single coating. Alternatively, the therapeutic agents may be compressed into the material of the sling 10, rather than being applied as a coating.

The therapeutic agents can be, for example, hydrophilic or hydrophobic. Hydrophilic drugs that may be employed in accordance with the invention include oxybutynin chloride, lidocaine, ketorolac, ketorolac tromethamine, which is available under the trade designation Toradol from Roche Pharmaceuticals (Nutley, N.J.) and hyoscyamine sulfate which is available under the trade designation CYTOSPAZ from Polymedica (Woburn, Mass.), for example. Suitable hydrophobic drugs include but are not limited to ibuprofen, ketoprofen, and diclofenac. The drug can be mixed with the coating and applied with the coating. Where the bonding between the coatings and drugs is weak, the drug that is absorbed will readily release to be delivered to the sides it contacts. Alternatively, a stronger bonding affinity may provide a slower timed release of the drug.

Where the coating applied to the surface of the sling 10 has an ionic charge, drugs comprising a complementary charge will bond to the coating when the coating and the drug are exposed to one another. The strength of any bonding will impact how readily the drug is released from the sling 10. Where the ionic bonding between the coating and the drug is weak, the drug will release more readily. In embodiments where rapid drug release is desirable, covalent bonding between the side coating and the drug should be avoided.

hi general, the therapeutic agent for use in connection with the present invention can be any pharmaceutically acceptable therapeutic agent. Preferred therapeutic agents include anti-inflammatory agents, analgesic agents, local anesthetic agents, antispasmodic agents, and combinations thereof.

Anti-inflammatory agents include steroidal and non-steroidal anti-inflammatory agents. Examples of non-steroidal anti-inflammatory drugs, include aminoarylcarboxylic acid derivatives such as enfenamic acid, etofenamate, flufenamic acid, isonixin, meclofenamic acid, mefanamic acid, niflumic acid, talniflumate, terofenamate and tolfenamic acid; arylacetic acid derivatives such as acemetacin, alclofenac, amfenac, bufexamac, cinmetacin, clopirac, diclofenac sodium, etodolac, felbinac, fenclofenac, fenclorac, fenclozic acid, fentiazac, glucametacin, ibufenac, indomethacin, isofezolac, isoxepac, lonazolac, metiazinic acid, oxametacine, proglumetacin, sulindac, tiaramide, tolmetin and zomepirac; arylbutyric acid derivatives such as bumadizon, butibufen, fenbufen and xenbucin; arylcarboxylic acids such as clidanac, ketorolac and tinoridine; arylpropionic acid derivatives such as alminoprofen, benoxaprofen, bucloxic acid, carprofen, fenoprofen, flunoxaprofen, flurbiprofen, ibuprofen, ibuproxam, indoprofen, ketoprofen, loxoprofen, miroprofen, naproxen, oxaprozin, piketoprofen, pirprofen, pranoprofen, protizinic acid, suprofen and tiaprofenic acid; pyrazoles such as difenamizole and epirizole; pyrazolones such as apazone, benzpiperylon, feprazone, mofebutazone, morazone, oxyphenbutazone, phenybutazone, pipebuzone, propyphenazone, ramifenazone, suxibuzone and thiazolinobutazone; salicylic acid derivatives such as acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamine o-acetic acid, salicylsulfuric acid, salsalate and sulfasalazine; thiazinecarboxamides such as droxicam, isoxicam, piroxicam and tenoxicam; others such as e-acetamidocaproic acid, s-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole and tenidap; and pharmaceutically acceptable salts thereof.

Examples of steroidal anti-inflammatory agents (glucocorticoids) include 21-acetoxyprefnenolone, aalclometasone, algestone, amicinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumehtasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol priopionate, halometasone, halopredone acetate, hydrocortamate, hydrocortisone, loteprednol etabonate, mazipredone, medrysone, meprednisone, methyolprednisolone, mometasone furoate, paramethasone, prednicarbate, prednisolone, prednisolone 25-diethylaminoacetate, prednisone sodium phosphate, prednisone, prednival, prednylidene, rimexolone, tixocortal, triamcinolone, triamcinolone acetonide, triamcinolone benetonide, triamcinolone hexacetonide, and pharmaceutically acceptable salts thereof.

Analgesic agents include narcotic and non-narcotic analgesics. Narcotic analgesic agents include alfentanil, allylprodine, alphaprodine, anileridine, benzylmorphine, bezitramide, buprenorphine, butorphanol, clonitazene, codeine, codeine methyl bromide, codeine phosphate, codeine sulfate, desomorphine, dextromoramide, dezocine, diampromide, dihydrocodeine, dihydrocodeinone enol acetate, dihydromorphine, dimenoxadol, dimepheptanol, dimethylthiambutene, dioxaphetyl butyrate, dipipanone, eptazocine, ethoheptazine, ethylmethlythiambutene, ethylmorphine, etonitazene, fentanyl, hydrocodone, hydromorphone, hydroxypethidine, isomethadone, ketobemidone, levorphanol, lofentanil, meperidine, meptazinol, metazocine, methadone hydrochloride, metopon, morphine, myrophine, nalbuphine, narceine, nicomorphine, norlevorphanol, normethadone, normorphine, norpipanone, opium, oxycodone, oxymorphone, papaveretum, pentazocine, phenadoxone, phenazocine, pheoperidine, piminodine, piritramide, proheptazine, promedol, properidine, propiram, propoxyphene, rumifentanil, sufentanil, tilidine, and pharmaceutically acceptable salts thereof.

Non-narcotic analgesics include aceclofenac, acetaminophen, acetaminosalol, acetanilide, acetylsalicylsalicylic acid, alclofenac, alminoprofen, aloxiprin, aluminum bis(acetylsalicylate), aminochlorthenoxazin, 2-amino-4-picoline, aminopropylon, aminopyrine, ammonium salicylate, amtolmetin guacil, antipyrine, antipyrine salicylate, antrafenine, apazone, aspirin, benorylate, benoxaprofen, benzpiperylon, benzydamine, bermoprofen, brofenac, p-bromoacetanilide, 5-bromosalicylic acid acetate, bucetin, bufexamac, bumadizon, butacetin, calcium acetylsalicylate, carbamazepine, carbiphene, carsalam, chloralantipyrine, chlorthenoxazin(e), choline salicylate, cinchophen, ciramadol, clometacin, cropropamide, crotethamide, dexoxadrol, difenamizole, diflunisal, dihydroxyaluminum acetylsalicylate, dipyrocetyl, dipyrone, emorfazone, enfenamic acid, epirizole, etersalate, ethenzamide, ethoxazene, etodolac, felbinac, fenoprofen, floctafenine, flufenamic acid, fluoresone, flupirtine, fluproquazone, flurbiprofen, fosfosal, gentisic acid, glafenine, ibufenac, imidazole salicylate, indomethacin, indoprofen, isofezolac, isoladol, isonixin, ketoprofen, ketorolac, p-lactophenetide, lefetamine, loxoprofen, lysine acetylsalicylate, magnesium acetylsalicylate, methotrimeprazine, metofoline, miroprofen, morazone, morpholine salicylate, naproxen, nefopam, nifenazone, 5' nitro-2' propoxyacetanilide, parsalmide, perisoxal, phenacetin, phenazopyridine hydrochloride, phenocoll, phenopyrazone, phenyl acetylsalicylate, phenyl salicylate, phenyramidol, pipebuzone, piperylone, prodilidine, propacetamol, propyphenazone, proxazole, quinine salicylate, ramifenazone, rimazolium metilsulfate, salacetamide, salicin, salicylamide, salicylamide o-acetic acid, salicylsulfuric acid, salsalte, salverine, simetride, sodium salicylate, sulfamipyrine, suprofen, talniflumate, tenoxicam, terofenamate, tetradrine, tinoridine, tolfenamic acid, tolpronine, tramadol, viminol, xenbucin, zomepirac, and pharmaceutically acceptable salts thereof.

Local anesthetic agents include amucaine, amolanone, amylocaine hydrochloride, benoxinate, benzocaine, betoxycaine, biphenamine, bupivacaine, butacaine, butaben, butanilicaine, butethamine, butoxycaine, carticaine, chloroprocaine hydrochloride, cocaethylene, cocaine, cyclomethycaine, dibucaine hydrochloride, dimethisoquin, dimethocaine, diperadon hydrochloride, dyclonine, ecgonidine, ecgonine, ethyl chloride, beta-eucaine, euprocin, fenalcomine, fomocaine, hexylcaine hydrochloride, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine hydrochloride, phenol, piperocaine, piridocaine, polidocanol, pramoxine, prilocaine, procaine, propanocaine, proparacaine, propipocaine, propoxycaine hydrochloride, pseudococaine, pyrrocaine, ropavacaine, salicyl alcohol, tetracaine hydrochloride, tolycaine, trimecaine, zolamine, and pharmaceutically acceptable salts thereof.

Antispasmodic agents include alibendol, ambucetamide, aminopromazine, apoatropine, bevonium methyl sulfate, bietamiverine, butaverine, butropium bromide, n-butylscopolammonium bromide, caroverine, cimetropium bromide, cinnamedrine, clebopride, coniine hydrobromide, coniine hydrochloride, cyclonium iodide, difemerine, diisopromine, dioxaphetyl butyrate, diponium bromide, drofenine, emepronium bromide, ethaverine, feclemine, fenalamide, fenoverine, fenpiprane, fenpiverinium bromide, fentonium bromide, flavoxate, flopropione, gluconic acid, guaiactamine, hydramitrazine, hymecromone, leiopyrrole, mebeverine, moxaverine, nafiverine, octamylamine, octaverine, oxybutynin chloride, pentapiperide, phenamacide hydrochloride, phloroglucinol, pinaverium bromide, piperilate, pipoxolan hydrochloride, pramiverin, prifinium bromide, properidine, propivane, propyromazine, prozapine, racefemine, rociverine, spasmolytol, stilonium iodide, sultroponium, tiemonium iodide, tiquizium bromide, tiropramide, trepibutone, tricromyl, trifolium, trimebutine, n,n-1trimethyl-3,3-diphenylpropylamine, tropenzile, trospium chloride, xenytropium bromide, and pharmaceutically acceptable salts thereof.

Two particularly preferred therapeutic agents for the practice of the present invention are (a) ketorolac and pharmaceutically acceptable salts thereof (e.g., the tromethamine salt thereof, sold under the commercial name Toradol®) and (b) 4-diethylamino-2-butynylphenylcyclohexylglycolate and pharmaceutically acceptable salts thereof (e.g., 4-diethylamino-2-butynylphenylcyclohexylglycolate hydrochloride, also known as oxybutynin chloride, sold under the commercial name Ditropan®).

The amount of the therapeutic agent present in the polymeric matrix is an amount effective to reduce the pain or discomfort associated with the medical device. Typically, the therapeutic agent is present in a polymeric matrix in a range from about 0.1% to about 30% by weight of the polymeric matrix (including 0.1%, 0.2%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30% and ranges between any two of these points, for instance, 0.1-10%, 10-20% and 20-30%, etc.).

Where the oxybutynin chloride and ketorolac tromethamine are used a range of 2-20% is typical, more typically 5-15%.

Alternatively, other therapeutic agents as known to those in the field as useful to enhance the efficacy of the sling 10 or reduce adverse reactions to the sling 10, for example, are contemplated with respect to the invention.

After placing the envelope 20 and sling 10 combination at the anatomical site, the operator withdraws the envelope 20 from the patient's body. The method of envelope 20 withdrawal may vary according to the various envelope 20 constructions. In some embodiments, the envelope 20 may be withdrawn from the body without being torn. In other embodiments, the operator tears or cuts the envelope 20 prior to withdrawal.

In one illustrative embodiment, the envelope 20 of FIGS. 1A, 1H and 1K includes a first sleeve 20A, a second sleeve 20B, tabs 188, 198, tab accesses 153A, 153B, 163A and 163B and the envelope hinge 200. The tabs 188 and 198 are internal tabs enclosed within the envelope 20. The tab 188 may be accessed from the inside of the envelope 20 and pulled outside the envelope 20 via the tab access 153A. The envelope 20 encloses the sling 10. The tab accesses 153A and 153B simplify accessing the tabs 188 and 198 to enable withdrawal of envelope 20.

Referring to FIGS. 1B and 1C, sleeve 20A, includes an inner surface 30, an outer surface 40, a proximal end 154, a distal end 150, a first lumen 185A, a tab 188 coupled to a top section 150A, and a bottom section 150B. The sleeve 20A further includes the tab access 153A.

Figure 1F:
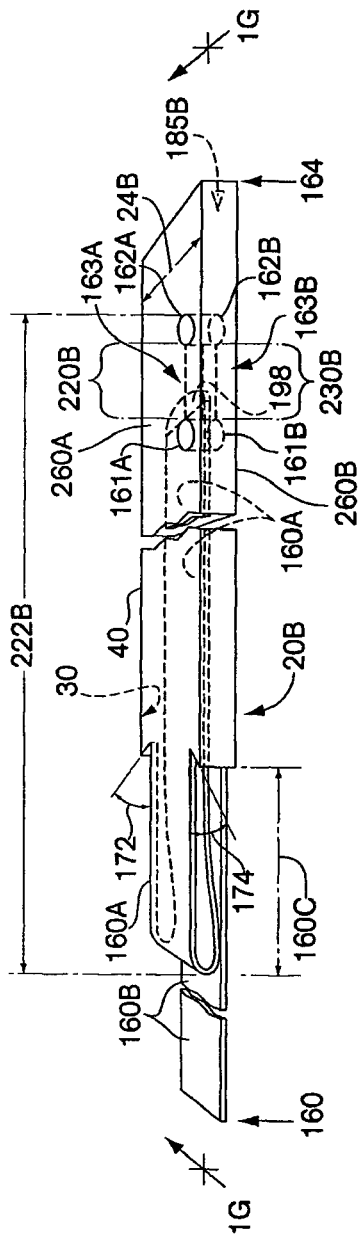
FIG. 1F illustrates another embodiment of one of the sleeves illustrated in FIG. 1A.

As shown in FIGS. 1B-1E, the tab access 153A and 153B may be one or more cuts 220A and 230A, respectively, disposed through a surface or a tearable region 222A of a sleeve 20A of envelope 20. The tearable region 222A includes a material that is easily torn open. Such easily torn materials include, but are not limited to, a material with a molecular orientation such as a linear low density polyethylene or linear polytetrafluoroethylene. The envelope 20 may be manufactured partially or entirely from these materials. For example, the envelope 20 may include sections including linear low density polyethylene along with sections including a series of perforations, cuts or apertures. Referring to FIGS. 1A, 1D and 1F, the envelope 20 includes a tearable region 222A and 222B with tabs 188 and 198, respectively, that may be torn away.

In one illustrative embodiment, referring again to FIGS. 1B-1D, the tab access 153A is formed from one or more perforations, apertures or cuts 220A that are disposed lengthwise along the length of the top surface 250A of the first sleeve 20A of envelope 20. In another exemplary embodiment (not shown) the tab access 153A may be placed transverse or at another angle relative to the length of a sleeve 20A of envelope 20.

In one illustrative embodiment, illustrated in FIGS. 1B-1D the tab access 153A includes the series of cuts 220A disposed on the top surface 250A along the length of sleeve 20A between one aperture, a first hole 151A, and another aperture, a second hole 152A. In another illustrative embodiment, the tab access 153B includes the series of cuts 230A disposed on the bottom surface 250B between one aperture, the first hole 151B, and another aperture, the second hole 152B. The diameter of the holes 151A, 152A, 151B and 152B may range between about 1/64 inches and about 1/4 inches, preferably being about 3/32 inches. In the illustrative embodiment, the sleeve 20A top surface 250A and bottom surface 250B have tab accesses 153A and 153B respectively. In another embodiment, either the top surface 250A or the bottom surface 250B of sleeve 20A has a tab access 153A or 153B.

FIGS. 1A, 1D and 1E illustrate another illustrative embodiment of the sleeve 20A of assembly 120. The tab 188 is coupled to the top section 150A and pulled into the first lumen 185A of sleeve 20A. In one illustrative embodiment, the tab 188 is positioned in the first lumen 185A between the first hole 151A and the second hole 152A of tab access 153A. In one embodiment, sleeve 20A has two first holes 151A and 151B, two second holes 152A and 152B, and the tab 188. Referring now to FIG. 1E, the first holes 151A and 151B may be positioned between about 0.5 inch to about 2 inches, preferably about 1.5 inches from the proximal end 154 of sleeve 20A. Each of the first holes 151A and 151B may be positioned at the same distance, or, alternatively, at different distances from the proximal end 154. The second holes 152A and 152B may be positioned between about 0.05 inch to about 1 inch, preferably about 0.5 inch from the proximal end 154 of sleeve 20A. Each of the second holes 152A and 152B may be positioned at the same distance, or, alternatively, at different distances from the proximal end 154. The tab 188 that is coupled to top section 150A and pulled into the first lumen 185A of sleeve 20A may be positioned between about 0.25 inch to about 1.75 inch, preferably about 1 inch from the proximal end 154 of sleeve 20A.

Figure 1G:
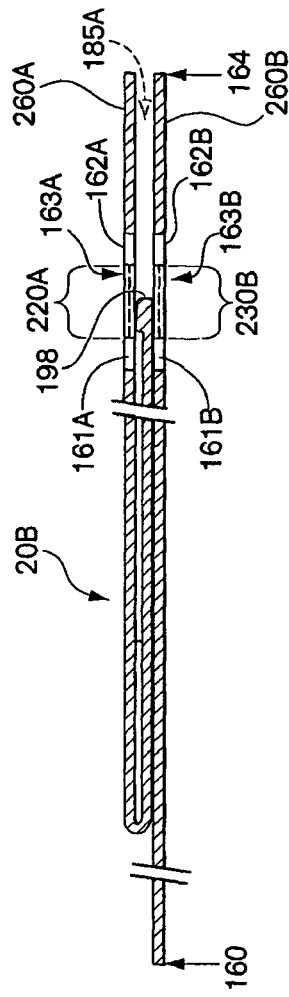
FIG. 1G illustrates a cross section at 1G-1G of the embodiment of the sleeve illustrated in FIG. 1F.

FIG. 1F illustrates a second sleeve 20B of the envelope 20 shown in FIG. 1A. For example, FIGS. 1F and 1G illustrate the sleeve 20B including an inner surface 30, an outer surface 40, a proximal end 160, a distal end 164, a second lumen 185B, a tab 198 coupled to a top section 160A, and a bottom section 160B. The sleeve 20B further includes the tab accesses 163A and 163B. The tab access 163A is formed from one or more perforations, apertures or cuts 220B disposed lengthwise along the length of the top surface 260A of sleeve 20B. Similarly, the tab access 163B is formed from one or more perforations, apertures or cuts 230B that are disposed lengthwise along the length of the bottom surface 260B of sleeve 20B. The tab accesses 163A and 163B may be placed transverse or at another angle relative to the length of sleeve 20B of envelope 20.

In one illustrative embodiment, the tab access 163A includes a series of cuts 220B disposed on the top surface 260A lengthwise along the length of sleeve 20B between one aperture, a first hole 161A, and another aperture, a second hole 162A. The tab access 163B includes a series of cuts 230B disposed on the bottom surface 260B lengthwise along the length of sleeve 20B between one aperture, a first hole 161B, and another aperture, a second hole 162B. The diameter of the holes 161A, 162A, 161B and 162B may range between about 1/64 inches and about 1/4 inches, preferably about 3/32 inches. In one embodiment, either the top surface 260A or the bottom surface 260B of sleeve 20B has a tab access 163A or 163B. In another embodiment, the tab 198 is coupled to the top section 160A and is pulled into the second lumen 185B of sleeve 20B such that the tab 198 is positioned in the second lumen 185B between the first holes 161A and 161B and the second holes 162A and 162B.

FIGS. 1F and 1G illustrate the sleeve 20B having two first holes 161A and 161B, two second holes 162A and 162B and the tab 198. Referring now to FIG. 1G, the first holes 161A and 161B may be positioned between about 0.5 inch to about 2 inches, preferably about 1.5 inches from the distal end 164 of sleeve 20B. Each of the first holes 161A and 161B may be positioned at the same distance, or, alternatively, at different distances from the distal end 164 of sleeve 20B. The second holes 162A and 162B may be positioned between about 0.05 inch to about 1 inch, preferably about 0.5 inch from the distal end 164 of sleeve 20B. Each of the second holes 162A and 162B may be positioned at the same distance, or, alternatively, at different distances from the distal end 164. The tab 198 that is coupled to top section 160A and pulled into the second lumen 185B of sleeve 20B may be positioned between the first holes 161A and 161B and the second holes 162A and 162B. In one embodiment, the tab 198 is positioned between about 0.25 inch to about 1.75 inch, preferably 1 inch from the distal end 164 of sleeve 20B. Referring now to FIGS. 1A, 1H, and 1K, the tab accesses 153A and 153B are positioned at the first end 201 of the envelope 20 and the tab accesses 163A and 163B are positioned at the second end 202 of envelope 20.

Referring now to FIG. 1H, the bottom section 150B of the first sleeve 20A is placed at about a 90° angle relative to the length of the first sleeve 20A. Similarly, the bottom section 160B of the second sleeve 20B is placed at about a 90° angle relative to the length of the second sleeve 20B. The sleeves 20A and 20B are aligned in proximity to one another such that the bottom sections 150B and 160B of sleeves 20A and 20B, respectively, face one another. Referring now to FIGS. 1A and 1K, the bottom sections 150B and 160B act as hinge sections when the bottom sections 150B and 160B are joined to one another by adhesive, staples, heat bonding or other means known to the skilled person to form hinge 200. In one embodiment, a clip (not shown) may be employed to join the bottom sections 150B and 160B, forming hinge 200.

As shown in FIG. 1I, the sleeves 20A and 20B form envelope 20 and the proximal end 154 of first sleeve 20A is positioned on the opposite end from the distal end 164 of the second sleeve 20B. The tab access 153A is located at a first end 201 of the envelope 20 and the tab access 163A is located at the second end 202 of the envelope 20. The tabs 188 and 198 are located at the first end 201 and the second end 202, respectively, of the envelope 20. The tab 188 is passed through the lumen 185A of sleeve 20A and is placed at the first end 201 of envelope 20 about the region of the tab access 153A and the tab 198 is passed through the lumen 185B of sleeve 20B and is placed at the second end 202 of envelope 20 about the region of the tab access 163A. Referring again to FIG. 1K, the bottom sections 150B and 160B of sleeve 20A and sleeve 20B form the hinge 200 of the envelope 20. The envelope 20 has a proximal end 154 and a distal end 164, formed by the proximal end 154 and distal end 164 of sleeves 20A and 20B, respectively. Referring again to FIG. 1I, the length of envelope 20, from the proximal end 154 to the distal end 164 ranges between about 4.0 inches to about 28.0 inches, or between about 12.0 inches and about 24.0 inches, most preferably 20.0 inches.

Referring now to FIGS. 1D, 1F and 1K, in a particular embodiment, the top section 150A is not fully pulled into the sleeve 20A, such that an overlap region 150C of the top section 150A remains on the outer surface 40. Similarly, the top section 160A of sleeve 20B is not fully pulled into the sleeve 20B, such that an overlap region 160C of top section 160A remains on the outer surface 40. The overlap regions 150C and 160C range between about 0.04 inches to about 1.2 inches, preferably about 0.3 inches. The overlap region 160C of sleeve 20B of envelope 20 may lay on top of the overlap region 150C of sleeve 20A of envelope 20. The overlap regions 150C and 160C protect the sling 10 enclosed within envelope 20. For example, in embodiments of the invention where the envelope 20 is employed to implant a mid-urethral sling 10, the overlap regions 150C and 160C of the envelope 20 prevents the sling 10 from stretching caused by, for example, a hemostat inadvertently applied to the sling 10 during surgery.

In one embodiment, referring now to FIGS. 1D, 1F and 1K, the tab accesses, 153A, 153B, 163A and 163B or a portion of a tab access, for example one or more hole 151A, 152A, 151B and 152B and/or one or more cut 220A, 220B, 230A, and 230B may be employed to sterilize envelope 20 and/or the sling 10 enclosed therein. In one embodiment, ethylene oxide (ETO) gas is supplied to the lumen 185 of envelope 20 through a portion of or the entire tab access 153A, 153B, 163A or 163B. In one illustrative embodiment, ETO is be supplied into the first hole 151B of envelope 20 prior to operator placement inside the patient's body.

In one illustrative embodiment, referring now to FIG. 1J, a placement fork 170 is employed to position an implant, such as a sling 10, within envelope 20. The placement fork 170 has a fork handle 173 and fork prongs 171. In one embodiment, the placement fork 170 has one or more fork prongs 171. In another embodiment, the placement fork 170 has two or more fork prongs 171. The fork prongs 171 may be configured to have a pointed end 175. Alternatively, the fork prongs 171 may be configured with a flat end 175. In one embodiment, the fork prongs 171 are configured with a rounded end 175. In other embodiments, a fork prong 171 has a sharp end 175 or a dull end 175. Placement forks 170 may have multiple fork prongs 171 having different configurations.

In one embodiment, referring to FIGS. 1I, 1J and 1K, the placement fork 171 is employed to place a sling 10 for treatment of female urinary incontinence in sleeves 20A and 20B of envelope 20. Each of sleeves 20A and 20B measure 9.75 inches and the sling 10 measures 18 inches. The length of each fork prong 171 may range from about 0.300 inch to about 0.400 inch, preferably about 0.350 inch long. The diameter of each fork prong 171 may measure between about 0.028 inch to about 0.040 inch, preferably about 0.030 inch. In one embodiment, there are two fork prongs 171 on the placement fork 170. In another embodiment, each fork prong 171 is spaced from about 0.090 inch to about 0.110 inch, preferably about 0.100 inch from the adjacent fork prong 171 on the placement fork 170. In one embodiment, the fork prongs 171 have rounded ends 175. The fork handle 173 length may range from about 10 inches to about 12 inches, preferably about 11 inches long.

The placement fork 170, including the handle 173 and fork prongs 171, may be configured to fit within the lumen 185 of envelope 20. The fork handle 173 and the fork prongs 171 of the placement fork 170 may be fabricated from various materials, including medical grade stainless steel, for example 304 stainless tool steel, or medical grade plastic, for example nylon or TEFLON®. In one embodiment, a material, such as a soft plastic, may be employed to cover the placement fork 170 handle 173 to provide ease of gripping and/or comfort to the operator using the placement fork 170.

Optionally, referring still to FIGS. 1J and 1K, when placing a sling 10, the overlap region 160C is pulled in the direction perpendicular to the envelope 20 and the overlap region 150C is pulled out of the lumen 185B of second sleeve 20B in the direction perpendicular to the envelope 20. The placement fork 170 may be held by the fork handle 173. The fork prongs 171 may be used to position the sling 10 inside envelope 20. The placement fork 170 may have one or more fork prongs 171. In one embodiment, the positioning fork 170 has two fork prongs 171.

In one illustrative embodiment, the implant, a sling 10, is pierced by the fork prongs 171 and positioned in the lumen 185B of second sleeve 20B of envelope 20. Thereafter, the sling 10 is positioned in the lumen 185A of first sleeve 20A of envelope 20. In another embodiment, the prongs 171 of the placement fork 170 are employed to position the sling 10 within the lumen 185B of the second sleeve 20B and within the lumen 185A of the first sleeve 20A, without piercing the sling 10. To ensure proper sling 10 placement within the lumen(s) 185A and 185B of the sleeves 20A and 20B, respectively, the length of the handle 173 of placement fork 170 may be selected according to the combined lengths of the sleeves 20A and 20B.

Referring again to FIG. 1K, the overlap regions 150C and 160C, cover the sling 10 enclosed within envelope 20. In another illustrative embodiment according to the invention, referring to FIG. 1K, the sling 10 is placed within the envelope 20 after the bottom sections 150B and 160B of sleeves 20A and 20B are joined to form hinge 200. Referring now to FIG. 1A, the tabs 208 and 218 are joined to the envelope 20 after the hinge 200 is formed. The tabs 208 and 218 are external to the envelope 20 and they are positioning members for positioning the envelope 20 inside the body of the patient. The tabs 208 and 218 are positioned at the proximal end 154 and the distal end 164 of envelope 20, respectively. The implant, for example the sling 10, may be manually inserted into lumen 185 of envelope 20. Alternatively, the sling 10 may be inserted into lumen 185 with the aid of a placement fork 170 described above with reference to FIG. 1J.

In another illustrative embodiment, referring to FIGS. 1K and 1J, the sling 10 is manually placed within the first lumen 185A of the first sleeve 20A and/or placed with the aid of the placement fork 170 or a grasping device, such as, for example, forceps. Thereafter, sleeve 20B is joined with the sleeve 20A to form the envelope 20, including the hinge 200. The remaining portion of the sling 10 may be placed within the second lumen 185B of sleeve 20B prior to or after forming the hinge 200.

In yet another embodiment, referring to FIGS. 1D, 1F and 1K the sling 10 is placed, via the tab accesses, 153A, 153B, 163A, and 163B, within the envelope 20 after the sleeves 20A and 20B are joined at hinge 200. According to this embodiment, referring also to FIGS. 1A and 1J, the sling 10 is inserted into, for example, cut 230B of tab access 163B manually and/or with the aid of a grasping device or the placement fork 170 and the sling 10 is positioned within lumen 185. In another embodiment, the sling 10 is placed within the envelope 20 via the tab accesses, 153A, 153B, 163A, and/or 163B after the sleeves 20A and 20B are joined at hinge 200, and after tabs 208 and 218 are joined to the envelope 20.

Figure 1L:
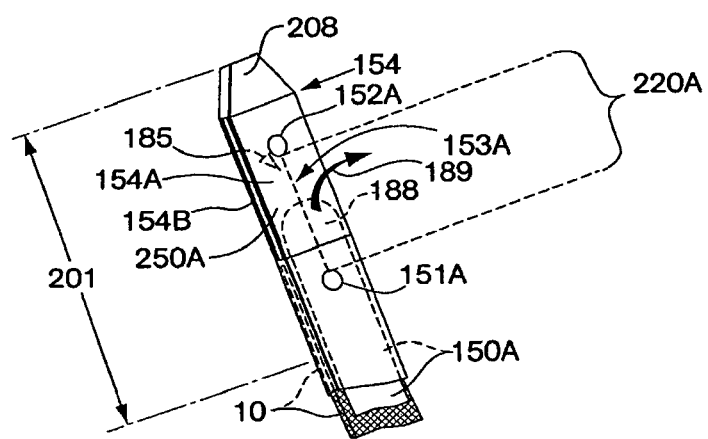
FIG. 1L illustrates an embodiment of a portion of the assembly for delivering an implant to a body illustrated in FIG. 1A.
Figure 1M:
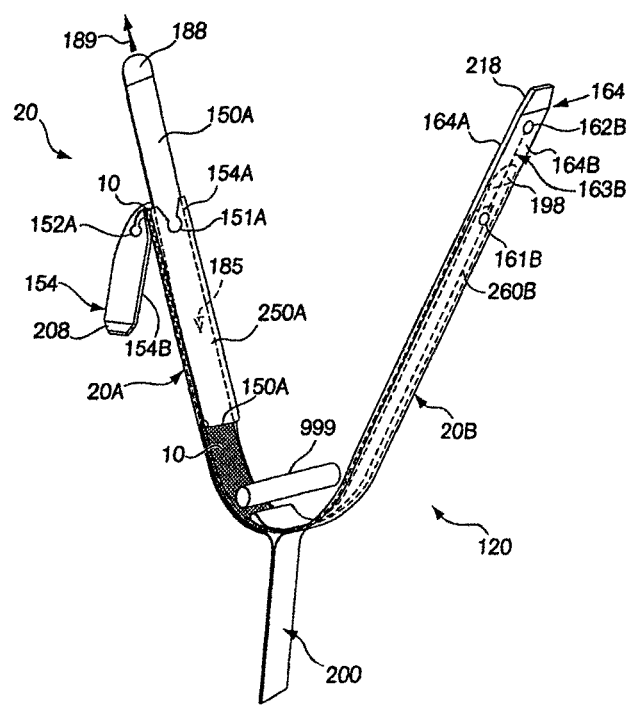
FIG. 1M illustrates another embodiment of the assembly for delivering an implant to a body illustrated in FIG. 1A.

With reference to FIGS. 1L-1M, in another aspect the invention includes a method for positioning the sling 10 at an anatomical site in the body of a patient. According to one embodiment of this method of the invention, the operator positions the assembly 120 of the envelope 20 enclosing sling 10 at the anatomical site, for example, the urethra 999 or bladderneck of a female patient. Referring to FIG. 1L, the tab 188 and the tab access 153A are located at the first end 201 of the envelope. The operator accesses the tab 188 by pulling tab 188 through cut 220A of tab access 153A. Referring to FIG. 1M, the operator intravaginally grasps hinge 200 and simultaneously pulls the tab 188 in the direction indicated by arrow 189. The force exerted on tab 188 coupled to the top section 150A tears the envelope 20 along the top surface 250A of the first sleeve 20A. Thereafter, the top section 150A of sleeve 20A is torn away from the envelope 20 in a single piece to expose the implant sling 10. Tab 188, the top section 150A, the top of sleeve 20A, and a portion of the proximal top section 154A are torn away from the envelope 20 and the implant sling 10 is exposed. The exposed portion of the sling 10 is adjacent the urethra 999.

Referring again to FIGS. 1A, 1F, 1I, 1K, and 1M, the operator similarly accesses tab 198 by pulling tab 198 through cut 220B of tab access. 163A. The tab 198 and the tab access 163A are located at the second end 202 of the envelope 20. The operator intravaginally grasps hinge 200 and simultaneously pulls tab 198. The force exerted on tab 198 coupled to the top section 160A tears the envelope 20 along the top surface 260A of the sleeve 20B away from the envelope 20. The force exerted on tab 198 coupled to the top section 160A tears these portions of sleeve 20B away from the envelope 20. Thus, tab 198, the top section 160A, the top of sleeve 20B, and a portion of the distal top section 164A are withdrawn from envelope 20. The portion of the sling 10 previously enclosed by the envelope 20 is thereby exposed. Finally, the hinge 200 and the remainder of envelope 20 including the tabs 208 and 218 are withdrawn via the patient's vagina. The sling 10 remains inside the body of the patient at the anatomical site where the operator positioned the sling 10, for example, at the anatomical site of the urethra 999.

Figure 2A:
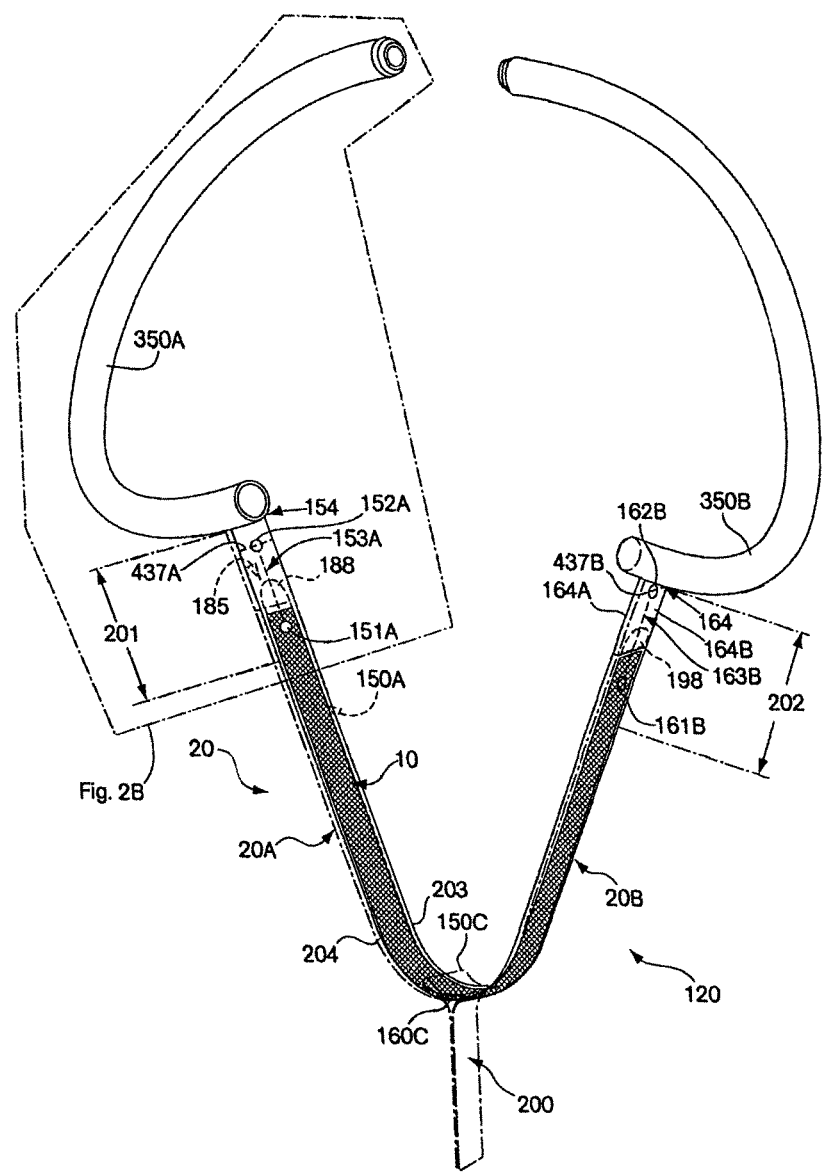
FIG. 2A illustrates another embodiment of an assembly for delivering an implant to a body.
Figure 2B:
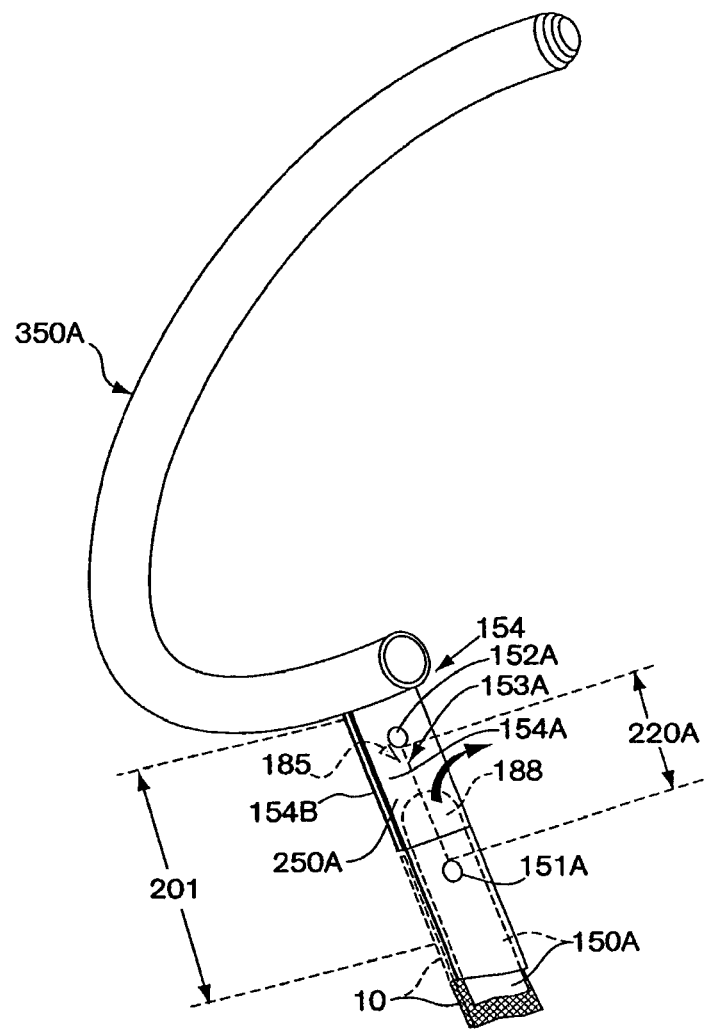
FIG. 2B illustrates another embodiment of a portion of the assembly for delivering an implant to a body illustrated in FIG. 2A.
Figure 2C:
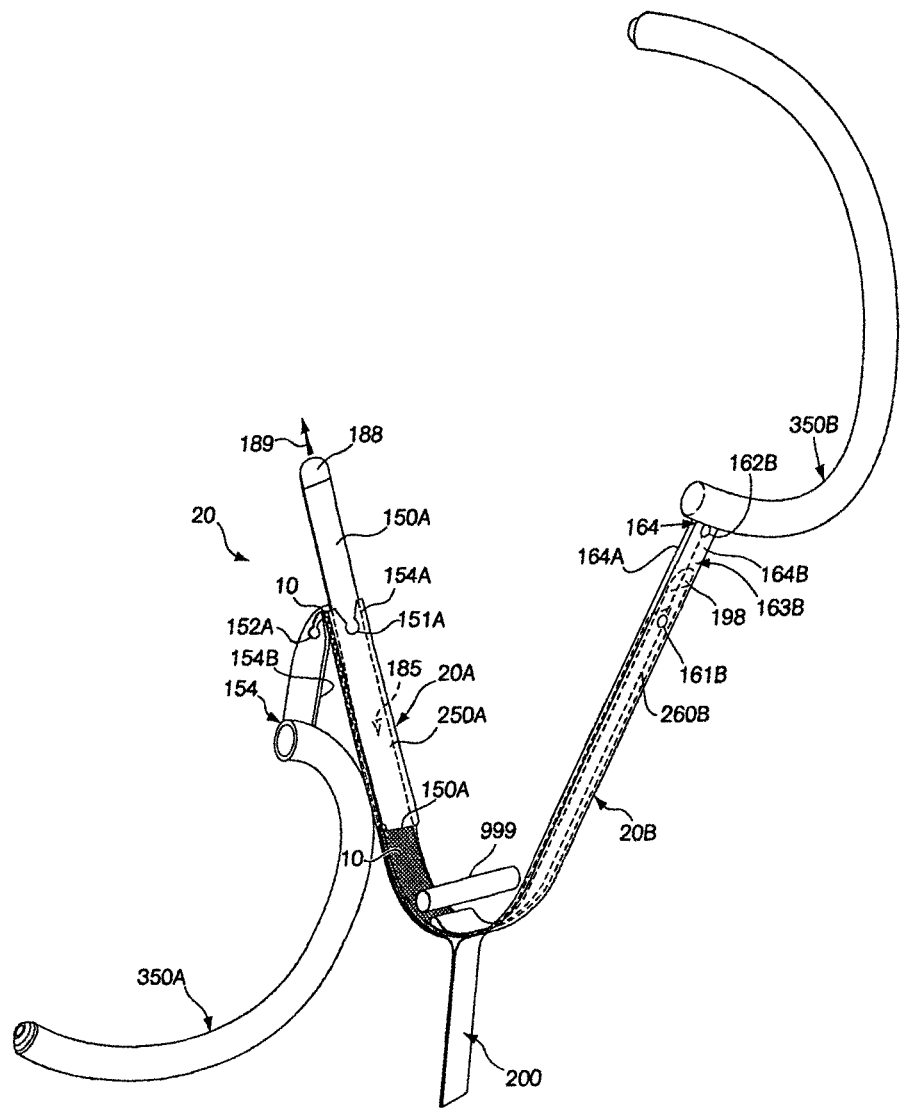
FIG. 2C illustrates another embodiment of an assembly for delivering an implant to a body illustrated in FIG. 2A.

In another illustrative embodiment, FIGS. 2A-2C illustrate the envelope 20, described in accordance with FIGS. 1A-1M, further including a first guide tube 350A and a second guide tube 350B. As illustrated in FIGS. 1K and 2A the assembly 120 includes the envelope 20 including first sleeve 20A, second sleeve 20B, tabs 188, 198, tab accesses 153A, 153B, 163A, and 163B, the envelope hinge 200, the envelope 20 enclosing all or part of sling 10. A first guide tube 350A is coupled to the proximal end 154 of first sleeve 20A and the second guide tube 350B is coupled to the distal end 164 of the second sleeve 20B of envelope 20. The first guide tube 350A, the proximal end 154, and the tab access 153A and the second guide tube 350B, the distal end 164, and the tab access 163A are positioned on opposite ends of the envelope 20 formed by sleeve 20A and sleeve 20B. The tab access 153A and 153B are positioned at the first end 201 of the envelope 20 and the tab accesses 163A and 163B are positioned at the second end 202 of the envelope 20.

The guide tubes 350A and 350B facilitate interoperability of the assembly 120 with a delivery device. Other structures that facilitate interoperability of the assembly 120 with a delivery device to introduce the assembly 120 to the body of the patient may be employed in accordance with the assembly 120 of the invention. Suitable configurations and structures include, for example, loops, apertures, male and/or female connectors, guide tubes and the like. Such other structures that may be employed are described in more detail in the U.S. patent application Ser. Nos. 10/093,371, 10/093,398, 10/093, 424, 10/093,450, 10/093,498, and 10/094,352 filed in the United States Patent Office on Mar. 7, 2002, which are based on and claim priority to provisional patent application Ser. No. 60/274,843 filed in the United States Patent Office on Mar. 9, 2001 and provisional patent application Ser. No. 60/286,863 filed in the United States Patent Office on Apr. 26, 2001, provisional patent application Ser. No. 60/418,827 filed in the United States Patent Office on Oct. 15, 2002, provisional patent application Ser. No. 60/418,642 filed in the United States Patent Office on Oct. 15, 2002, provisional patent application Ser. No. 60/434,167 filed in the United States Patent Office on Dec. 17, 2002, U.S. patent application Ser. No. 10/325,125 filed Dec. 19, 2002, provisional patent application Ser. No. 60/449,465 filed in the United States Patent Office on Feb. 24, 2003, provisional patent application Ser. No. 60/465,722 filed in the United States Patent Office on Apr. 25, 2003, and U.S. patent application Ser. No. 10/832, 653 filed Apr. 26, 2004, entitled "Systems and Methods for Sling Delivery and Placement" by Chu et al. filed on even date herewith, the entirety of all of which are incorporated herein by reference.

Referring to FIGS. 2A-2C, the operator may employ the assembly 120 of the invention to position the implant at an anatomical site in the body of a patient. The operator will employ the first and second guide tube 350A and 350B to position the envelope 20 enclosing sling 10 at an anatomical site in the body of a patient. Other structures as described and incorporated herein above may be used to position the envelope 20 enclosing sling 10 at an anatomical site in the body of a patient. The envelope 20 may be positioned with the aid of a delivery device that may be employed to access the patient's urethra 999 according to supra-pubic, pre-pubic, transvaginal, or transobturator approaches. The operator positions the envelope 20 enclosing sling 10, at the anatomical site, for example, the urethra 999 or bladderneck. Referring to FIG. 2B, the operator accesses the tab 188 by pulling tab 188 through cut 220A of tab access 153A. Referring to FIG. 2C, the operator intravaginally grasps hinge 200 and simultaneously pulls the tab 188 in the direction indicated by arrow 189. The force on tab 188 coupled to the top section 150A tears the envelope 20 along the top portion of the first sleeve 20A. Thereafter, the top section 150A of sleeve 20A is torn away from the envelope 20 in a single piece to expose the implant sling 10. Tab 188, the top section 150A, the top surface 250A of sleeve 20A, and a portion of the proximal top section 154A are torn away from the envelope 20 and the implant sling 10 is exposed. The exposed portion of the sling 10 is adjacent the urethra 999.

Referring now to FIGS. 1K, 1F and 2C, the operator similarly accesses tab 198 by pulling tab 198 through cut 220B of tab access 163A. The operator intravaginally grasps hinge 200 and simultaneously pulls tab 198. The force exerted on tab 198 coupled to the top section 160A tears these portions of sleeve 20B away from the envelope 20. Thus, tab 198, the top section 160A, the top surface 260A of sleeve 20B, and a portion of the distal top section 164A are withdrawn from envelope 20. The portion of the sling 10 previously enclosed is thereby exposed. Finally, the hinge 200 and the remainder of envelope 20 including the first guide tube 350A and the guide tube 350B are withdrawn via the patient's vagina. The sling 10 remains inside the body of the patient at the anatomical site where the operator positioned the sling 10, for example, at the anatomical site of the urethra 999.

Referring now to FIGS. 1D, 2B and 2C, in another illustrative embodiment, the tab accesses 153A and 153B include perforations (not shown) about the perimeter of the perpendicular axis 24A of sleeve 20A of envelope 20. The operator can access the tab 188 by grasping and withdrawing, for example, the guide tube 350A and the portion of the envelope 20 lying between the perforation and the envelope 20 proximal end 154. The tab 188 is thereby exposed and is accessible to the operator. In one embodiment, the envelope 20 tab access 153A has perforations about the perimeter of the perpendicular axis 24A of envelope 20 and also has a nick (not shown) at one or more portions of the perforated perimeter that enables the tab access 153A to be pulled or torn to expose the tab 188 enclosed within the envelope 20.

In yet another embodiment, referring now to FIGS. 1I, 1K, and 2A the tab access 153A and 153B includes shapes (not shown) cut out of one or more of the top surfaces 250A, 260A and bottom surfaces 250B, 260B of sleeves 20A and 20B, respectively. Suitable cut out shapes include, oval and triangle, and the triangular cut out shape may have, for example, rounded edges.

Referring now to FIGS. 1D, 1F, and 2A, in one illustrative embodiment for positioning the assembly 120 in the body of a patient, the envelope 20 enclosing an sling 10 is positioned inside the body of a patient. The tab access 153A, including a cut 220A disposed between the first hole 151A and the second hole 152A, and the tab access 153B, including a cut 230A disposed between the first hole 151B and the second hole 152B, are cut at position 437A. The cut at position 437A cuts through the second holes 152A and 152B. The guide tube 350A and a portion of the envelope material are withdrawn. Thereafter, the sides of envelope 20 sleeve 20A are pulled apart by opening and separating each of the cuts 220A and 230A. In one embodiment, the sides of envelope 20 separate until the point where the first holes 151A and 151B are located. The first holes 151A and 151B may provide, for example, relief to the cuts 220A and 230A.

In another illustrative embodiment, tab accesses 163A, 163B on sleeve 20B are cut at position 437B and tab 198 is similarly accessed by separating the sides of the envelope 20. The guide tube 350B and a portion of the envelope are withdrawn.

According to this embodiment, after the sling 10 is positioned, the operator cuts the envelope 20 at position 437A, withdraws the first guide tube 350A, and separates the envelope 20 to provide accesses to the tab 188. The operator intravaginally grasps hinge 200 and simultaneously pulls the tab 188 and the force on tab 188 coupled to the top section 150A tears the envelope 20 along the top portion of the first sleeve 20A. The top section 150A of sleeve 20A is torn away from the envelope 20 in a single piece to expose the implant sling 10. Tab 188, the top section 150A, the top surface 250A of sleeve 20A, and a portion of the proximal top section 154A are torn away from the envelope 20 and the implant sling 10 is exposed. The exposed portion of the sling 10 is adjacent the anatomical site The operator cuts the envelope 20 at position 437B, withdraws the second guide tube 350B, and separates the envelope 20 to provide accesses to the tab 198. The operator grasps hinge 200 and simultaneously pulls tab 198. The force exerted on tab 198 coupled to the top section 160A tears these portions of sleeve 20B away from the envelope 20. Thus, tab 198, the top section 160A, the top surface 260A of sleeve 20B, and a portion of the distal top section 164A are withdrawn from envelope 20. The portion of the sling 10 previously enclosed is thereby exposed. Finally, the hinge 200 and the remainder of envelope 20 are withdrawn via the vagina. This embodiment avoids guide tubes 350A and 350B being pulled back through the patient's body when the operator withdraws the remainder of the envelope. The sling 10 remains inside the body of the patient at the anatomical site where the operator positioned the sling 10.

Referring again to FIG. 2A, in another embodiment, the tab access 153A and 153B is a cut out shape, for example, an oval (not shown). In one embodiment, the cut out oval may be cut over positions 437A and 437B. When the operator cuts positions 437A, 437B withdrawing a portion of the envelope 20 and first guide tube 350A and a portion of the envelope 20 and a second guide tube 350B. The portion of the envelope 20 below positions 437A and 437B may be separated until the point at the bottom of the oval, providing access to the tabs 188, 198 enclosed within the envelope 20.

In another aspect, the invention includes an assembly 120 for delivering the envelope 20 and an implant, for example, a sling 10 to an anatomical site in the body of a patient. In one embodiment, shown in FIG. 3A, the assembly 120 includes the envelope 20 including two or more sleeves 20A, 20B, one or more tabs 208, 218 and a tongue 155. The tongue 155 simplifies placement and/or withdrawal of the envelope 20 from inside the body of the patient and prevents damage to the sling 10 thereby maintaining the integrity of the sling 10 enclosed by the envelope 20.

Figure 3A:
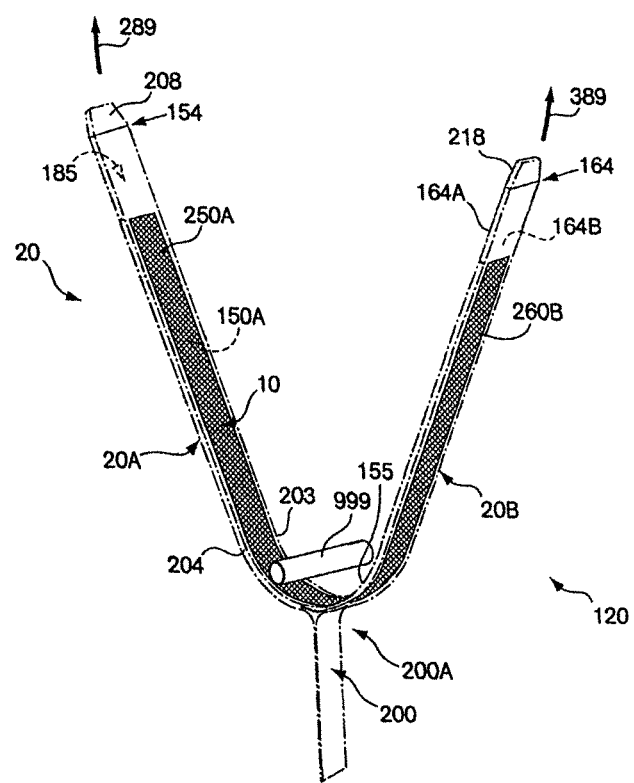
FIG. 3A illustrates one embodiment of an assembly for delivering an implant to a body.
Figure 3B:
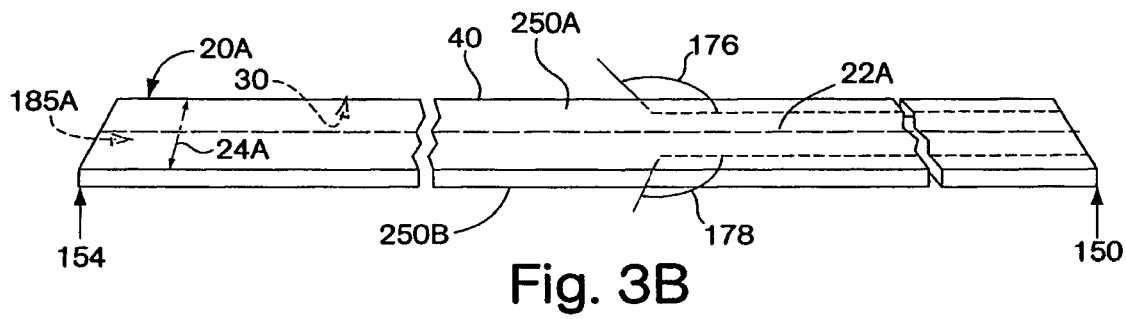
Figure 3C:
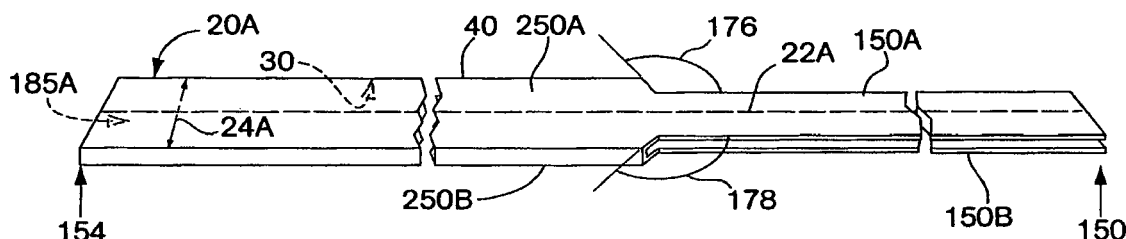
Figure 3D:
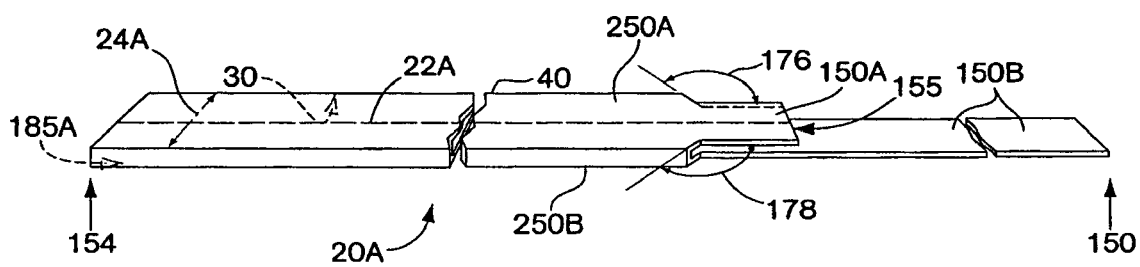

Referring to FIG. 3D, generally, the tongue 155 is an extension of the top section 150A of the sleeve 20A. The tongue 155 extends from one end of the sleeve 20A. In one embodiment, the tongue 155 is separate, i.e., non-contiguous with the bottom section 150B of the sleeve 20A. In another embodiment, tongue 155 extends from the top section 150A beyond the lumen 185A of the sleeve 20A. The tongue may be flexible and it may be any flat shape, for example, rectangular or oval. The length of the tongue measures between about 0.2 inches and about 5 inches, preferably about 1 inch in length. The width of the tongue measures between about 0.1 inches and about 2.0 inches. The thickness of the tongue 155 is at least as thick as the sleeve from which the tongue is made. In another embodiment, the tongue 155 is bonded at an end of sleeve 20A, in such embodiments the tongue 155 thickness may be greater, less, or equal to the thickness of the sleeve 20A to which the tongue 155 is bonded. The tongue 155 may be bonded to sleeve 20A by adhesives, sutures, or heat bonding as well as by other bonding means known to the skilled person.

Referring now to FIG. 3B, in one embodiment of the invention, the tongue is made by cutting two angles into the first sleeve 20A, as indicated by the arrow 176 and arrow 178. The angles 176 and 178 are cut in the range of from about 40° to about 170°, or about 80° to about 130°, preferably about 110°, from the longitudinal axis 22A of the sleeve 20A illustrated in FIG. 3B. Preferably, the angles 176 and 178 are obtuse, ranging from greater than 90° to about 130° as measured from the longitudinal axis 22A on the side of the distal end 150 of the sleeve 20A. In one embodiment, the two angles 176 and 178 are cut into the first sleeve 20A for a distance between about 0.01 inch and about 0.05 inch, preferably about 0.04 inch into the sleeve 20A as measured along the perpendicular axis 24A. Referring now to FIGS. 3A and 3D, the angles 176 and 178 and the depth of the cut into the sleeve 20A along the perpendicular axis 24A at which the angles 176 and 178 are placed, determines the placement of tongue 155 of envelope 20, by, for example, sizing or placing the tongue 155 to cover the sling 10 enclosed by envelope 20.

Referring to FIG. 3C, the distal end portion 150 of sleeve 20A is trimmed along the longitudinal axis 22A from the distal end 150 to angle 176 and from the distal end 150 to the angle 178. In general, the amount of the first sleeve 20A that is trimmed along the longitudinal axis 22A from the distal end 150 to each respective angle 176 and 178 is substantially the same. The first sleeve 20A has a first lumen 185A, and its structure is tube-like, and after the first sleeve 20A is trimmed, the distal end 150 portion has a top section 150A and a bottom section 150B. After the first sleeve 20A is trimmed, the longitudinal axis 22A of first sleeve 20A from the angle 178 to the end 150 of top section 150A, may measure between about 2.0 inches to about 14.0 inches, preferably about 10.0 inches. As illustrated in FIG. 3D, the top section 150A is trimmed along the perpendicular axis 24A forming a tongue 155 which measures between about 0.2 inches and about 5 inches, preferably about 1 inch in length as measured along the longitudinal axis 22A of envelope 20. The envelope 20 may be trimmed by employing, for example, a razor. The width of the tongue 155 measured along the perpendicular axis 24A of envelope 20, is sized so that it is equal to or smaller than the inner diameter of a second lumen 185B of the second sleeve 20B of envelope 20, illustrated in FIG. 3F. For example, the width of the tongue 155 may measure between about 0.1 inches and about 2.0 inches.

Figure 3E:
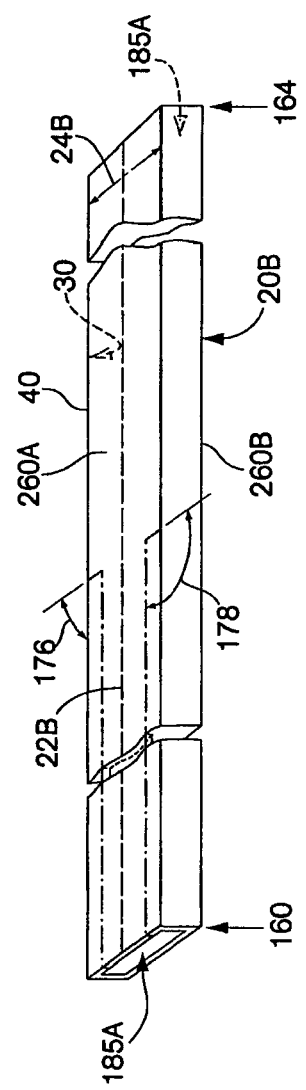
Figure 3F:
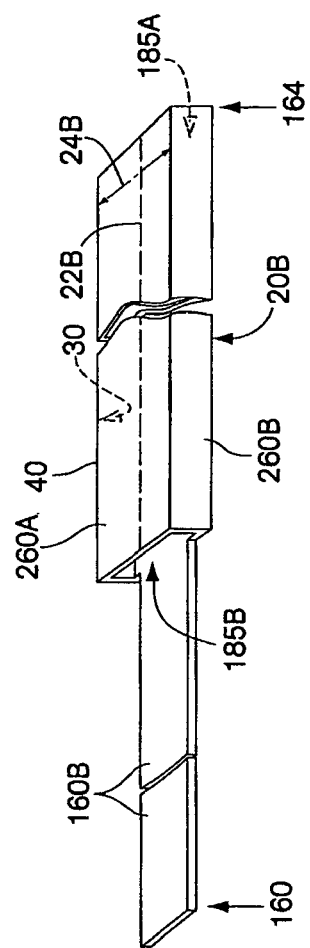

Referring now to FIGS. 3E and 3F, the second sleeve 20B of the envelope 20 shown in FIG. 3A is illustrated. Referring to FIG. 3E, the second sleeve 20B has the inner surface 30, the outer surface 40, the proximal end 160, and the distal end 164. The second sleeve 20B includes the second lumen 185B. The length of the second sleeve 20B between the proximal end 160 and the distal end 164, along the longitudinal axis 22B, is between about 4.0 inches and about 28.0 inches, preferably about 20.0 inches. The perpendicular axis 24B of second sleeve 20B measures between about 0.2 inches to about 2.0 inches, preferably between about 0.4 inches and about 0.8 inches, preferably about 0.6 inches.

Still referring to FIG. 3E, the two angles 176, 178, are cut into the second sleeve 20B in the range of about 40° to about 170°, or about 80° to about 130°, preferably about 90° from the longitudinal axis 22B of second sleeve 20B proximal end 160. In one embodiment, the two angles 176 and 178 are cut into the second sleeve 20B for a distance between about 0.01 inch and about 0.05 inch, preferably about 0.04 inch into the sleeve 20A as measured along the perpendicular axis 24B. The second sleeve 20B is trimmed along the longitudinal axis 22B from the proximal end 160 to the angle 176 and from the proximal end 160 to the angle 178. In general, the amount of the second sleeve 20B that is trimmed along the longitudinal axis 22B from the proximal end 160 to each respective angle, 176 and 178, is substantially the same. The second sleeve 20B second lumen 185B includes a tube-like structure. Referring now to FIGS. 3E and 3F, after the tube-like second sleeve 20B is trimmed, the proximal end 160 includes a top section and a bottom section 160B. Referring now to FIG. 3F, the longitudinal axis 22B of second sleeve 20B from the angle 176 and the angle 178 to the end of bottom section 160B may measure between about 2.0 inches to about 14.0 inches, preferably about 10.0 inches. The top section is trimmed along the perpendicular axis 24B of sleeve 20B, from the legs of angles 176 and 178, which are at an angle to the longitudinal axis 22B of sleeve 20B.

As shown in FIGS. 3D, 3F, and 3G, the bottom section 150B of the first sleeve 20A is placed at about a 90° angle relative to the longitudinal axis 22A of the first sleeve 20A. Similarly, the bottom section 160B of the second sleeve 20B is placed at about a 90° angle relative to longitudinal axis 22B of the second sleeve 20B. The sleeves 20A and 20B are aligned in proximity to one another such that the bottom sections 150B and 160B of sleeves 20A and 20B, respectively, face one another.

Referring now to FIG. 3I, the bottom sections 150B and 160B are joined to one another by adhesive, staples, heat bonding or other means known to the skilled person to form hinge 200. In one embodiment, a clip (not shown) may be employed to join bottom sections 150B and 160B, which act as hinge sections when they form hinge 200. As shown in FIG. 3H, the proximal end 154 of first sleeve 20A and the distal end 164 of the second sleeve 20B are positioned on opposite ends of the envelope 20 formed by sleeve 20A and sleeve 20B. The length of envelope 20, measured along the longitudinal axis 22 from proximal end 154 to the distal end 164, ranges between about 4.0 inches to about 28.0 inches, or between about 12.0 inches and about 24.0 inches, most preferably 20.0 inches.

Referring again to FIG. 3I, the tongue 155 of the first sleeve 20A is tucked inside the lumen 185B of the second sleeve 20B. The tongue 155 is sized and shaped so that it fits within the lumen 185B of the second sleeve 20B. When the tongue 155 is tucked inside lumen 185B, the sling 10 enclosed within envelope 20 is shielded by the tongue 155 in the region 255 of the envelope 20 corresponding to the tongue 155. For example, in embodiments where the envelope 20 is employed to implant a mid-urethral sling 10, the tongue 155 of the envelope 20 prevents damage to the sling 10 caused by, for example, patient tissue rubbing against the sling 10 in the region of the envelope 20 corresponding to the tongue 155 during sling 10 placement. Also, the tongue 155 prevents abrasion to patient tissue caused by the sling 10 during envelope 20 placement.

Referring to FIGS. 3A and 3D, in another embodiment, two sleeves 20A, each having a tongue 155, are provided. The two sleeves 20A are positioned so that their tongues 155 face one another and are positioned on the same plane. Each sleeve 20A tongue 155 is configured to fit inside the lumen 185A of sleeve 20A that it faces. According to this embodiment, the two sleeve 20A tongues 155 combine to provide the desired coverage and protection of the sling 10 enclosed within the envelope 20. In one illustrative embodiment, referring, still to FIGS. 3A and 3D, two sleeves 20A having a perpendicular axis 24A measuring about 1 inch may be identically cut to provide a tongue 155 width that measures about 0.5 inch, as measured from angle 178 along the perpendicular axis 24A. The two sleeves 20A are positioned so that their tongues 155 face one another and are positioned on the same plane. Each of the two sleeves 20A tongue 155 is inserted into the lumen 185A of the sleeve 20A that it faces and the two tongues 155 protect a sling 10 enclosed by the two sleeves 20A when they form an envelope 20.

As shown in FIGS. 3A and 3G-3I, and as described above, sleeves 20A and 20B are joined to form envelope 20. The first lumen 185A and the second lumen 185B form the single lumen 185 of the envelope 20. The joined bottom sections 150B and 160B of sleeves 20A and 20B act as hinge sections to form hinge 200 of envelope 20. Various methods may be employed to join bottom sections 150B and 160B, for example, heat bonding, adhesives, or staples. In one embodiment, a clip (not shown) may be employed to join bottom sections 150B and 160B, forming hinge 200. The length of hinge 200 may range between about 2.0 inches to about 14.0 inches in length. The hinge 200 may be trimmed to a shorter length that may be grasped by the operator during the method of delivering the implant assembly, described below. One or both of sleeves 20A and 20B of envelope 20 may be made from a composite of two or more materials.

In another aspect, the invention is a method for delivering an implant assembly 120 to a patient's body. Referring to FIGS. 3H-3I, the sling 10 is placed within the envelope 20 as is described above with reference to FIGS. 1J and 1K. At least a portion of the sling 10 is enclosed within the envelope 20 and in one embodiment, the envelope 20 encloses substantially all of the sling 10. With reference to FIG. 3A, in another aspect the invention is a method for positioning an implant, for example, a sling 10 at an anatomical site in the body of a patient. According to one embodiment of this method of the invention, the operator positions the envelope 20 enclosing sling 10, at the anatomical site, for example, the urethra 999 or bladderneck.

With reference to FIGS. 3A and 3I, the operator grasps hinge 200 and cuts hinge 200 near position 200A. Position 200A is the area of the hinge 200 adjacent implant sling 10, where bottom sections 150B and 160B of sleeves 20A and 20B are not sealed. In one embodiment, the operator cuts one bottom section, 150B or 160B, at position 200A to free it from the other bottom section 150B or 160B. In another embodiment, the operator cuts hinge 200 at position 200A and thereafter withdraws hinge 200 via the vagina. In one embodiment, the joined bottom sections 150B and 160B of hinge 200 are pulled apart. In another embodiment, the operator unfastens and withdraws a clip (not shown) surrounding the bottom sections 150B and 160B, which act as hinge sections, that form hinge 200.

The operator next grasps tab 208 and pulls tab 208 and the attached sleeve 20A in the direction indicated by arrow 289, withdrawing the tab 208 and attached sleeve 20A. Thereafter, the operator grasps tab 218 and pulls tab 218 and the attached sleeve 20B in the direction indicated by arrow 389, withdrawing the tab 218 and attached sleeve 20B. The sling 10 previously enclosed by the envelope 20 is thereby exposed and the sling 10 remains inside the body of the patient at the anatomical site where the sling 10 was positioned by the operator, for example, at the anatomical site of the urethra 999.

Figure 4:
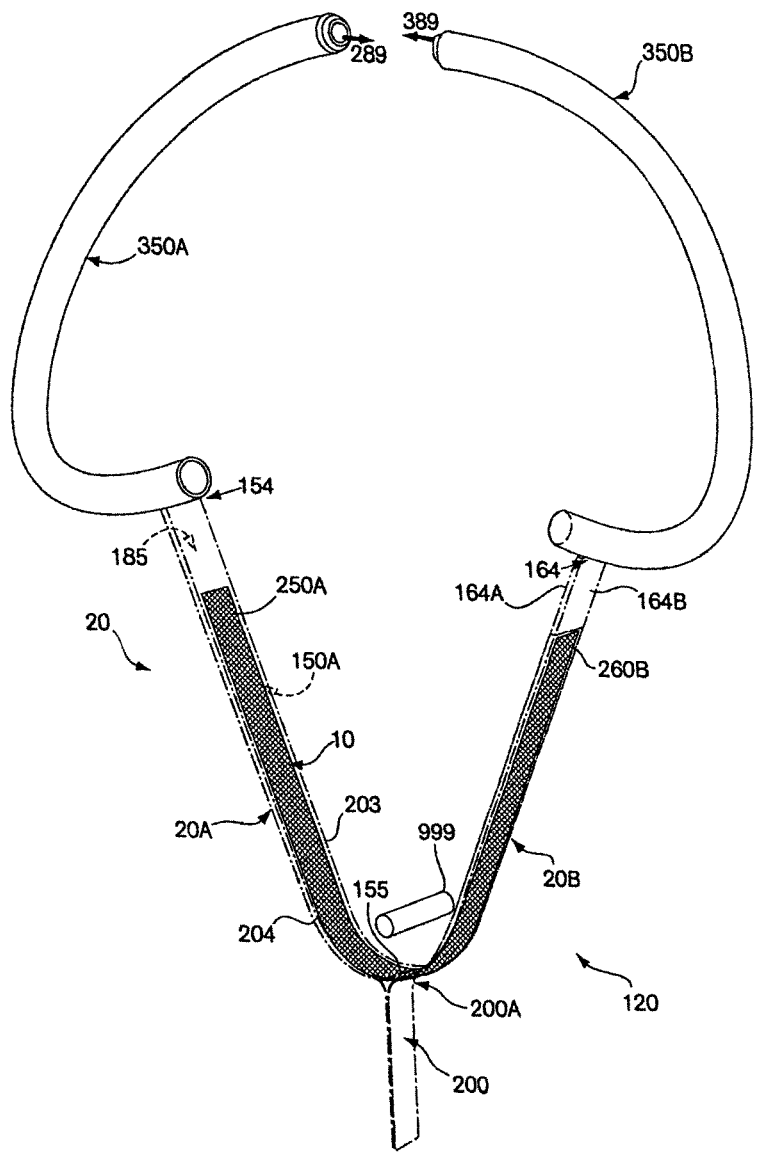
FIG. 4 illustrates another embodiment of an assembly for delivering an implant to a body.

FIG. 4 illustrates the envelope 20 having the tongue 155, as described above with reference to FIGS. 3A-3I, further including the first guide tube 350A and the second guide tube 350B, as described above with reference to FIGS. 2A-2C. The guide tubes 350A and 350B may provide the operator a mechanical advantage and simplify grasping and withdrawing the sleeves 20A and 20B during the surgical procedure to position the sling 10 at an anatomical site in the body of a patient, for example, at the urethra 999.

Figure 5A:
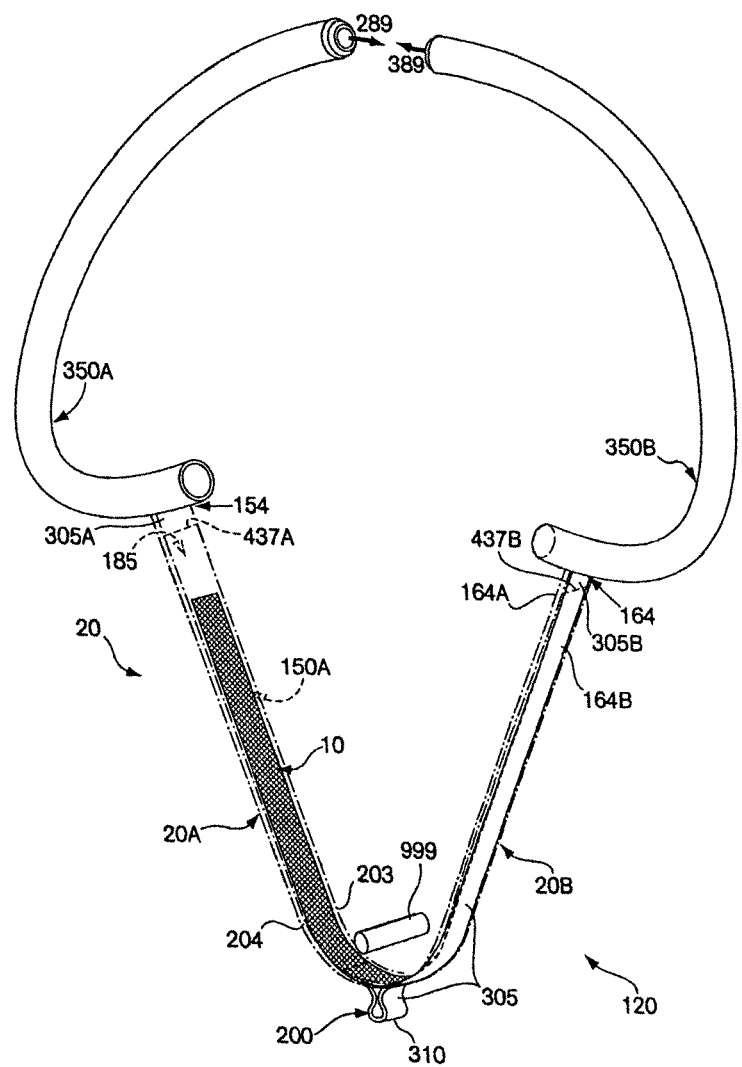
FIG. 5A illustrates one embodiment of an assembly for delivering an implant to a body.

In another aspect, the invention includes an assembly 120 for delivering an envelope 20 and an implant sling 10 to an anatomical site in the body of a patient. In one embodiment, shown in FIG. 5A the assembly 120 includes the envelope 20 including two or more sleeves 20A, 20B, one or more guide tubes 350A, 350B, and a scaffold 305. Referring also to FIG. 5I, the scaffold 305 joins sleeve 20A and 20B to form envelope 20. In one embodiment, the scaffold 305 has a fold 310 that is positioned, for example, between sleeves 20A and 20B. In one embodiment the fold 310 positioned between sleeves 20A and 20B forms a hinge 200. The scaffold 305 simplifies placement and/or withdrawal of the envelope 20 from inside the body of the patient and maintains the integrity of the envelope 20.

Referring now to FIGS. 5A-5G, the scaffold 305 generally is a flat piece of material that is dimensioned to fit within the lumens 185A and 185B of the sleeves 20A and 20B to join the sleeves 20A and 20B that form the envelope 20. The scaffold 305 may be fabricated from one or more materials such as, for example, polypropylene, polyethylene, polyester, polytetrafluoroethylene, TYVEK®, MYLAR®, and co-polymers thereof as well as one or more dissolvable materials or one or more absorbent materials such as, for example, a sponge-like material such as polyglycolic acid, polylactic acid and other suitable absorbable materials. The scaffold 305 may be firm or rigid, but preferably, it is flexible. Referring to FIG. 5C, the scaffold thickness may range from about 1 mil to about 6 mil, preferably about 3.5 mils. Referring to FIG. 5B, the scaffold 305 longitudinal axis 32 is measured from the scaffold 305 first side 305A to the scaffold second side 305B. The longitudinal axis 32 ranges between about 4 inches and about 60 inches, preferably being about 23 inches. The scaffold perpendicular axis 34 ranges between about 0.2 inches to about 2 inches, preferably between about 0.4 inches to about 0.8 inches, preferably being about 0.6 inches.

FIGS. 5A and 5D illustrate the scaffold 305 having a fold 310. The fold 310 may be employed to position an implant enclosed by envelope 20. The fold 310 may aid in withdrawal of the scaffold 305 or withdrawal of the envelope 20 after assembly 120 placement (described below). In one embodiment, a portion of the scaffold 305 longitudinal axis 32 is pinched to form a fold 310. Adhesives, staples, heat bonding or other bonding means known to the skilled person may be employed to maintain the fold 310 in the scaffold 305. The fold 310, as measured perpendicular to the longitudinal axis 32 of scaffold 305, ranges from about 0.5 inches to about 6 inches, preferably 2 inches long. In another embodiment, two or more pieces of material may be bonded together by adhesives, staples, heat bonding or other bonding means known to the skilled person to make scaffold 305 and the two pieces of material may form a bond joint to provide the fold 310.

Referring to FIG. 5A, the scaffold 305 thickness and the material used to manufacture the scaffold 305 may be selected to provide the envelope 20 with integrity appropriate for the surgical procedure, e.g., to withstand the forces imposed on the envelope 20 when placing the sling 10 in the patients body. In another embodiment, the scaffold 305 material may be selected because it forms a strong bond with the sleeve 20A, 20B or the guide tube 350A, 350B. The scaffold 305 material may be the same or different than the material used to manufacture the sleeves 20A, 20B. The scaffold 305 may be bonded inside the lumens 185A and 185B of the sleeves 20A and 20B by adhesives, suturing, heat bonding or any other means known to the skilled person. In one embodiment, the scaffold 305 is bonded to a portion of the sleeve 20A inside the lumen 185A.

Referring to FIG. 5A, in one embodiment according to the invention, the assembly 120 includes an envelope 20 including a first sleeve 20A, a second sleeve 20B, the scaffold 305 and a sling 10. Guide tubes 350A and 350B are disposed on the proximal end 154 and the distal end 164 of the envelope 20. Referring now to FIG. 5E, the sleeve 20A may have a tongue 155 prepared in the same manner as was described with respect to the FIGS. 3B-3D. Referring still to FIG. 5E, the bottom section 150B, described in relation to FIG. 3D, is removed by trimming the bottom section 150B along the perpendicular axis 24A of sleeve 20A. In one embodiment, the bottom section 150B of sleeve 20A is trimmed along the perpendicular axis 24A from about the angle 176 vertex to about the angle 178 vertex.

Figure 5F:
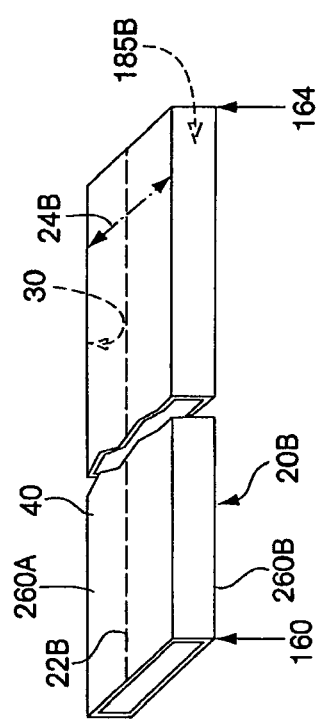
FIG. 5F illustrates another one of the sleeves for use in the assembly illustrated in FIG. 5A for delivering an implant to a body.

Referring to FIG. 5F, the second sleeve 20B of the envelope 20 shown in FIG. 5A is illustrated. The second sleeve 20B has an inner surface 30, an outer surface 40, a proximal end 160, and a distal end 164. The second sleeve 20B is a tube-like structure including a second lumen 185B. The length of the second sleeve 20B between the proximal end 160 and the distal end 164, along the longitudinal axis 22B, measures between about 2.0 inches and about 14.0 inches, preferably being about 10.0 inches. The perpendicular axis 24B of second sleeve 20B measures between about 0.2 inches to about 2.0 inches, preferably between about 0.4 inches and about 0.8 inches, preferably about 0.6 inches.

As illustrated in FIGS. 5G and 5I, the first side 305A of scaffold 305 is inserted into lumen 185A and the second side 305B of scaffold 305 is inserted into lumen 185B. The scaffold 305 may be bonded to a portion or along the entire length of the lumens 185A and 185B of sleeves 20A and 20B, respectively, by employing adhesive, staples, heat bonding or other means known to the skilled person. In another embodiment, the scaffold 305 is simply positioned inside the lumens 185A and 185B of the sleeves 20A and 20B without being bonded to the sleeves 20A or 20B of envelope 20. One or both of sleeves 20A and 20B may be made from a composite of two or more materials.

In one embodiment, referring now to FIGS. 5E and 5F, sleeve 20A, measured from the proximal end 154 to the end of the tongue 155 along the longitudinal axis 22A measures about 10.75 inches, with the length of tongue 155 measuring about 1 inch, and the longitudinal axis 22B of sleeve 20B measures about 9.75 inches. Referring again to FIG. 5I, in one embodiment, the scaffold 305 joins sleeves 20A and 20B to form envelope 20 and the sling 10 is positioned inside the lumen 185 of envelope 20. When the sleeve 20A tongue 155 is tucked inside the lumen 185B of sleeve 20B, the envelope 20 measures about 19.5 inches. In an embodiment where sling 10 measuring about 14 inches long is enclosed by envelope 20, about 5.5 inches of space of lumen 185 is free from the sling 10. The proximal end 154 and the distal end 164 of envelope 20 may each extend up to about 2 inches beyond the sling 10.

Referring now to FIGS. 5F and 5I, the scaffold 305 may be used to join two sleeves 20B and 20B that do not have a tongue 155. In such embodiments, a portion of the sling 10 enclosed by the envelope 20 may be exposed.

One or both of sleeves 20A and 20B of envelope 20 may be made from a composite of two or more materials. The scaffold 305 may or may not have a fold 310. Referring now to FIG. 5A, the scaffold 305 may be used to join sleeves 20A and 20B with or without guide tubes 350A and 350B. For example, in some embodiments, the scaffold 305 joins sleeves 20A and 20B having tabs (not shown).

In another illustrative embodiment according to the invention, referring again to FIG. 5A, the sling 10 is placed within the lumen 185 of envelope 20 after sleeves 20A and 20B are joined when scaffold 305 is positioned between the sleeves 20A and 20B, but prior to guide tubes 350A and 350B being joined to the envelope 20. A first guide tube 350A and a second guide tube 350B are described above with reference to FIGS. 2A-2C. Tabs 208 and 218 described with reference to FIGS. 1A and 3A may alternatively be joined to the envelope 20 proximal end 154 and distal end 164, respectively. The implant, for example a sling 10, may be inserted into the lumen 185 of envelope 20 manually and/or with the aid of a grasping device or with the aid of a placement fork 170 described above with reference to FIG. 1J. The envelope 20 may enclose at least a portion of the sling 10. In one embodiment, referring to FIG. 5I, the envelope 20 includes a tongue 155, which may be employed to overlay or protect the sling 10 enclosed within envelope 20.

Referring to FIGS. 1J and 5I, in one embodiment, the sling 10 inside lumen 185 lies between scaffold 305 and the top surfaces, 250A and 260A of the sleeves 20A and 20B of envelope 20. In another illustrative embodiment, at least the first end 305A of scaffold 305 is placed inside of the first lumen 185A of sleeve 20A and the sling 10 is placed within the first lumen 185A of the first sleeve 20A manually and/or with the aid of a grasping device or with the aid of a placement fork 170. Thereafter, sleeve 20B is joined with sleeve 20A by inserting at least the second end 305B of scaffold 305 inside the lumen 185B of sleeve 20B to form envelope 20. In one embodiment the first end 305A and the second end 305B of scaffold 305 are bonded inside the lumens 185A and 185B of the sleeves 20A and 20B, respectively. The remaining portion of sling 10 may be placed within the second lumen 185B of sleeve 20B. Optionally, the remaining portion of sling 10 may be placed within the second lumen 185B of sleeve 20B prior to or after forming a fold 310 within scaffold 305.

The operator may employ the assembly 120 of the invention illustrated in FIG. 5A to position the sling 10 at an anatomical site in the body of a patient. The operator will employ the first and second guide tubes 350A and 350B to position the envelope 20 enclosing sling 10 at an anatomical site in the body of a patient with the aid of a delivery device. Suitable delivery devices may be used to position the envelope 20 of the assembly 120 enclosing at least a portion of an implant according to a plurality of surgical approaches, for example, according to transvaginal, transabdominal (e.g., percutaneous), supra-pubic, pre-pubic, or transobturator approaches. The operator positions the envelope 20 enclosing sling 10 at the anatomical site, for example, the urethra 999 or bladderneck.

With continued reference to FIG. 5A, the operator grasps the scaffold 305 that is between the sleeves 20A and 20B and then cuts the scaffold 305. In one illustrative embodiment, the operator cuts and withdraws the fold 310 within the scaffold 305. Next, the operator grasps the first guide tube 350A and pulls guide tube 350A, the attached sleeve 20A, and a portion of scaffold 305 in the direction indicated by arrow 289, withdrawing the guide tube 350A, attached sleeve 20A and a portion of scaffold 305 from the patient's body. Thereafter, the operator grasps the second guide tube 350B and pulls guide tube 350B, the attached sleeve 20B and a portion of scaffold 305 in the direction indicated by arrow 389, withdrawing the guide tube 350B, the attached sleeve 20B and a portion of scaffold 305 from the patient's body. In one embodiment, the guide tubes 350A and 350B provide the operator with a mechanical advantage simplifying grasping the sleeves 20A and 20B during the surgical procedure. The sling 10 previously enclosed by the envelope 20 is thereby exposed and remains inside the body of the patient at the anatomical site where the sling 10 was positioned by the operator, for example, at the anatomical site of the urethra 999.

Referring still to FIG. 5A, in another illustrative embodiment, the operator cuts envelope 20 at position 437A and withdraws the first guide tube 350A and a portion of envelope 20. The operator cuts envelope 20 at position 437B and withdraws the second guide tube 350B and a portion of the envelope 20. According to this embodiment, the scaffold 305 may be bonded to the lumens 185A and 185B of envelope 20. The operator cuts the scaffold 305 and grasps and withdraws the first envelope 20A and a portion of scaffold 305 from the patient. Thereafter, the operator grasps and withdraws the second envelope 20B and a portion of scaffold 305 from the patient. The sling 10 previously enclosed by the envelope 20 is thereby exposed and remains inside the body of the patient at the anatomical site where the sling 10 was positioned by the operator, for example, at the anatomical site of the urethra 999.

In another embodiment, referring still to FIG. 5A, the guide tube 350A, the proximal end 154 of sleeve 20A and the scaffold 305 first end 305A are bonded together. Similarly, the guide tube 350B, the distal end 164 of sleeve 20B and the scaffold 305 second end 305B are bonded together. The operator cuts and withdraws guide tubes 350A and 350B at positions 437A and 437B on envelope 20. Thereafter, the operator grasps scaffold 305 between the sleeves 20A and 20B and intravaginally withdraws the scaffold 305 from the envelope 20. Optionally, the scaffold 305 fold 310 is grasped. Finally, the operator grasps and withdraws the first sleeve 20A and thereafter grasps and withdraws the second sleeve 20B. The sling 10 previously enclosed by the envelope 20 is thereby exposed and the sling 10 remains inside the body of the patient at the anatomical site where the sling 10 was positioned by the operator, for example, at the anatomical site of the urethra 999. Alternatively, after cutting the envelope 20 at positions 437A and 437B and withdrawing guide tubes 350A and 350B, the operator first grasps and withdraws the first sleeve 20A, then grasps and withdraws the second sleeve 20B, and finally grasps and withdraws the scaffold 305. In one embodiment, when the sleeves 20A and 20B are withdrawn from the patient prior to the scaffold 305, the scaffold 305 acts as a slide that enables the sleeves 20A and 20B to disengage from the envelope 20.

Referring to FIGS. 6-7, the implant assembly 120, and more specifically, the envelope 20 of the assembly 120 has a proximal end 154 and a distal end 164 and the envelope 20 encloses at least a portion of the implant, for example a sling 10 for treatment of female urinary incontinence. The implant sling 10 may be made from a mesh. Referring now to FIG. 6, in one embodiment, the envelope 20 includes a single sleeve 20C.

In one illustrative embodiment, the sling 10 includes a de-tanged mid-length portion 244, which has end points 249A and 249B, and two tanged end-length portions 248A and 248B. Suitable implant slings 10 include the de-tanged slings such as the slings described in, for example, U.S. Ser. No. 10/092,872 filed Mar. 7, 2002, the entirety of which is incorporated by reference herein. The two tanged end-length portions 248A and 248B extend from the end points 249A, 249B of the de-tanged mid-length portion 244 to sling ends 252A and 252B, respectively. The two tanged end-length portions 248A and 248B are, in a preferred embodiment, of substantially equal length, such that the de-tanged mid-length portion 244 is substantially centered along the long axis of the sling 10.

The envelope 20 includes a first sleeve surface 256 extending along the long axis of the envelope 20 and a second sleeve surface 258 disposed on the opposite side of the envelope 20 from the first sleeve surface 256. In one embodiment, the first sleeve surface 256 has at least one discontinuity 264. Referring to FIG. 6, for example, in one embodiment, the discontinuity 264 in the first sleeve surface 256 is, for example, a gap 268, indicated by double-ended arrows 269. The gap 268 is defined by a first sleeve end point 276A and a second sleeve end point 276B. Referring now to FIG. 7, in an alternative embodiment, the envelope 20 includes two discontinuities 264 in the first sleeve surface 256, for example, slit-shaped apertures 272A, 272B. In still other embodiments, the first sleeve surface 256, or the second sleeve surface 258, may include any number of discontinuities 264.

Referring to the embodiment illustrated in FIG. 6, a first region 273A in the first sleeve surface 256 extends from the proximal end 154 to the end point 276A and a second region 273B in the first sleeve surface 256 extends from the distal end 164 to the end point 276B. The separation of the first region 273A from the second region 273B by the gap 268 allows the envelope 20 to be removed when the physician cuts the second sleeve surface 258. The gap also aids in removal of the envelope 20 by preventing friction between the first region 273A and the second region 273B that might otherwise occur if the regions 273A and 273B overlapped. Friction between the regions 273A and 273B would make the process of removing the envelope 20 from about the sling 10 more difficult. The gap 268 eliminates the possibility that the first region 273A and the second region 273B may stick to one another.

The gap 268 in the first sleeve surface 256 may be made in a variety of ways. As an example, the envelope 20 is flattened and a rectangular window, having width substantially equal to the width of the first sleeve surface 256, is cut out of a mid-length section of the first sleeve surface 256.

Referring still to the embodiment illustrated in FIG. 6, the de-tanged mid-length portion 244 of the sling 10 is preferably in alignment with, and therefore exposed at, the gap 268. In other words, end points 249A, 249B of the de-tanged mid-length portion 244 preferably coincide with the first sleeve end point 276A and the second sleeve end point 276B, respectively.

Referring to the embodiment illustrated in FIG. 7, the sling 10 is shown to be at least partially enclosed by the envelope 20. The sling 10 exits the envelope 20 at one slit-shaped aperture 272A and 272B, and re-enters the envelope 20 at the other slit-shaped aperture 272B and 272A. Preferably, the end points 249A and 249B of the de-tanged mid-length portion 244 coincide with the slit-shaped apertures 272A and 272B of the first sleeve surface 256, such that the de-tanged mid-length portion 244 of the sling 10 is located outside the envelope 20, between the slit-shaped apertures 272A and 272B, and the two tanged end-length portions 248A and 248B are enclosed within the envelope 20.

Variations, modifications, and other implementations of what is described herein will occur to those of ordinary skill in the art without departing from the spirit and the scope of the invention. Accordingly, the invention is not to be defined only by the preceding illustrative description of certain embodiments.

What is claimed is:

1. A method for delivering an implant to an anatomical site in the body of a patient, the method comprising the steps of:
    providing an assembly comprising the implant and an envelope, said envelope comprising at least a first sleeve and a second sleeve, said sleeves configured to enclose at least a portion of said implant, said first sleeve comprising a tongue, wherein said tongue overlaps said implant and extends into said second sleeve, the implant being a sling;
    positioning said implant at said anatomical site; and
    withdrawing said envelope from the patient's body, the withdrawing including withdrawing at least a portion of said envelope from the patient's body via a vagina of the patient.

2. The method of claim 1 wherein each sleeve further comprises a hinge section, the hinge section of one sleeve coupled to the hinge section of the other sleeve.

3. The method of claim 2 further comprising:
    cutting said hinge sections, separating said first sleeve from said second sleeve and withdrawing said first and second sleeves from the patient's body.

4. A method for delivering an implant to an anatomical site in the body of a patient, the method comprising the steps of:
    providing an assembly comprising the implant and an envelope, said envelope comprising at least a first sleeve and a second sleeve, said first and second sleeves configured to enclose at least a portion of said implant, the implant being a sling;
    providing a scaffold comprising a folded portion, said folded portion forming a hinge extending at an angle away from a straight portion of said scaffold, said scaffold coupling said first sleeve and said second sleeve;
    positioning said implant at said anatomical site; and
    withdrawing said envelope from the patient's body, the withdrawing including withdrawing at least a portion of said envelope from the patient's body via a vagina of the patient.

5. The method of claim 4 further comprising the steps of:
    cutting said scaffold and separating said first sleeve and said second sleeve; and
    withdrawing said scaffold and said sleeves from the patient's body.

6. A method for delivering an implant to an anatomical site in the body of a patient, the method comprising the steps of:
    providing an assembly comprising the implant and an envelope, the implant being a sling, said envelope comprising at least two sleeves, said sleeves configured to enclose at least a portion of said implant, wherein each sleeve further comprises a hinge section, said hinge section of one sleeve coupled to said hinge section of the other sleeve to define a portion extending at an angle away from the implant;
    positioning said implant at said anatomical site in the patient's body; and
    withdrawing said envelope from the patient's body, the withdrawing including withdrawing at least a portion of said envelope from the patient's body via a vagina of the patient.

7. The method of claim 6 further comprising, prior to withdrawing said envelope from the patient's body, the step of:
    cutting said hinge section and separating said first and second sleeves.

8. A method for delivering an implant to an anatomical site in the body of a patient, the method comprising the steps of:
    positioning an implant at an anatomical location;
    pulling a tab in a first sleeve section to tear a portion of an envelope away from the implant; and
    intravaginally pulling on a hinge on the envelope subsequent to pulling on said tab to withdraw at least a portion of said envelope from the body via the vagina.

9. The method of claim 8 further comprising the steps of:
    accessing said tab on the first sleeve section via a tab access on the first sleeve section prior to pulling said tab.

* * * * *